United States Patent [19]
Kramer et al.

[11] Patent Number: 5,866,788
[45] Date of Patent: Feb. 2, 1999

[54] RECOMBINANT CHITINASE AND USE THEREOF AS A BIOCIDE

[75] Inventors: Karl J. Kramer; Subbaratnam Muthukrishnan, both of Manhattan, Kans.; Hee Kyung Choi, Kyungki-Do, Taiwan; Lolita Corpuz; Bhuvana Gopalakrishnan, both of Manhattan, Kans.

[73] Assignee: Kansas State University Research Foundation, Manhattan, Kans.

[21] Appl. No.: 524,051

[22] Filed: Sep. 6, 1995

Related U.S. Application Data

[63] Continuation-in-part of Ser. No. 224,987, Apr. 8, 1994, abandoned.

[51] Int. Cl.$^6$ .............................. A01H 5/00; C12N 15/12; C12N 15/56; C12N 15/82
[52] U.S. Cl. ........................ 800/205; 536/23.5; 435/69.1; 435/172.3; 435/200; 435/252.2; 435/320.1; 435/418; 435/419; 800/DIG. 43; 800/DIG. 55; 47/58
[58] Field of Search .......................... 536/23.5; 800/205, 800/DIG. 43, DIG. 55; 435/172.3, 320.1, 252.2, 200, 69.1, 418, 419; 935/57; 47/58

[56] References Cited

U.S. PATENT DOCUMENTS

| | | | |
|---|---|---|---|
| 4,870,023 | 9/1989 | Fraser et al. | 435/320.1 |
| 4,940,840 | 7/1990 | Suslow et al. | 800/205 |
| 5,071,748 | 12/1991 | Miller | 435/69.1 |
| 5,173,419 | 12/1992 | Harman et al. | 435/209 |

OTHER PUBLICATIONS

Metraux et al.; Isolation of a complementary DNA encoding a chitinase with structural homology to a bifunctional lysozyme/chitinase; Proc. Natl. Acad. Sci., vol. 86, pp. 896–900, Feb. 1989.

Kuranda et al.; Chitinase is required for cell separation during growth of *saccharomyces cerevisiae*, The Journal of Biological Chemistry, vol. 266, No. 29, Issue of 10/15, pp. 19758–19767, 1991.

Jones et al.; Isolation and characterization of genes encoding two chitinase enzymes from *Serratia marcescens*, EMBO Journal, vol. 5 No. 3, pp. 467–473, 1986.

Harpster et al Nucleic Acids Research, vol. 17, No. 13, 1989, p. 5395.

Robbins et al.; Primary structure of the Streptomyces enzyme Endo–β–N–acetylglucosaminidase H, The Journal of Biological Chemistry, vol. 259, No. 12, Issue of 6/25, pp. 7577–7583, 1984.

Kamei et al.; Amino Acid Sequence of Chitinase from *Streptomyces erythraeus*, J. Biochem, 105, 979–985 (1989).

Watanabe et al.; Chitinase System of *Bacillus circulans* WL–12 and Importance of Chitinase A1 in Chitin Degradation, Journal of Bacteriology, Jul. 1990, pp. 4017–4022, vol. 172, No. 7.

Watanabe et al. Structure of the Gene Encoding Chitinase D of *Bacillus circulans* WL–12 and Possible Homology of the Enzyme to Other Prokaryotic Chitinase sand Class III Plant Chitinases, Journal of Bacteriology, vol. 174, No. 2, Jan. 1992, pp. 408–414.

Samac et al.; Isolation and Characterization of the Genes Encoding Basic and Acidic Chitinase in *Arabidopsis thaliana*, Plant Physiol. (1990), 93, 907–914.

Broglie, et al.; Transgenic plants with enhanced resistance to the fungal pathogen *rhizoctonia solani*, Science, vol. 254, pp. 1194–1197, Nov. 22, 1991.

Kramer et al. 1993. Insect Biochem. Mol. Biol. 23(6):691–701.

Lewin, R. 1987. Science 237:1570.

Reeck et al. 1987. Cell 50:667.

Flach et al 1992 Experientia 48: 701–716.

Shapiro et al 1987 J. Econ. Entomology 80(6): 1113–1116.

St. Leger et al 1987 J. of Gen. Microbiol. 133: 1371–1382.

Krishnan et al 1994 (Aug.) J Biol. Chem. 269 (33): 20971–20976.

Smigocki et al 1993 Plant Molecular Biol 23: 325–335.

*Primary Examiner*—David T. Fox
*Attorney, Agent, or Firm*—Hovey, Williams, Timmons & Collins

[57] ABSTRACT

A recombinantly derived insect chitinase gene is inserted into a vector for host expression of the chitinase protein, and may be utilized according to methods for controlling a population of insect pests. A recombinant virus is provided for this purpose, as well as a recombinant plant. Recombinantly derived insect chitinase may also be expressed in host cells or larvae for subsequent purification.

31 Claims, 10 Drawing Sheets

```
GAATTCCCTC GCCGACACAC CGCTACGTTC AAA ATG CGA GCG ACA CTG GCG ACG        54
                                     Met Arg Ala Thr Leu Ala Thr
                                       1               5

TTG GCT GTC CTG GCC TTA GCG ACG GCG GTT CAA TCG GAC AGC AGA GCG        102
Leu Ala Val Leu Ala Leu Ala Thr Ala Val Gln Ser Asp Ser Arg Ala
            10              15                  20

CGC ATA GTA TGC TAC TTC AGC AAT TGG GCG GTG TAT CGG CCT GGT GTA        150
Arg Ile Val Cys Tyr Phe Ser Asn Trp Ala Val Tyr Arg Pro Gly Val
        25              30                  35

GGG CGG TAC GGC ATC GAG GAC ATT CCA GTG GAG AAG TGT ACC CAC ATC        198
Gly Arg Tyr Gly Ile Glu Asp Ile Pro Val Glu Lys Cys Thr His Ile
 40              45                  50                  55

ATT TAC TCC TTC ATT GGC GTC ACT GAG GGC AAC AGC GAA GTA CTT ATC        246
Ile Tyr Ser Phe Ile Gly Val Thr Glu Gly Asn Ser Glu Val Leu Ile
                60                  65                  70

ATT GAT CCT GAG TTG GAT GTA GAT AAG AAT GGT TTC CGC AAC TTT ACA        294
Ile Asp Pro Glu Leu Asp Val Asp Lys Asn Gly Phe Arg Asn Phe Thr
            75                  80                  85

TCG CTT CGG TCT TCG CAT CCC AGC GTC AAG TTC ATG GTA GCG GTG GGC        342
Ser Leu Arg Ser Ser His Pro Ser Val Lys Phe Met Val Ala Val Gly
        90                  95                 100

GGC TGG GCT GAA GGC AGT TCG AAG TAC TCT CAT ATG GTT GCA CAG AAG        390
Gly Trp Ala Glu Gly Ser Ser Lys Tyr Ser His Met Val Ala Gln Lys
    105                 110                 115

AGC ACC CGC ATG TCT TTT ATC AGG AGC GTT GTC AGT TTT CTC AAG AAG        438
Ser Thr Arg Met Ser Phe Ile Arg Ser Val Val Ser Phe Leu Lys Lys
120                 125                 130                 135

TAC GAC TTC GAC GGT CTA GAC CTT GAT TGG GAG TAC CCA GGA GCC GCT        486
Tyr Asp Phe Asp Gly Leu Asp Leu Asp Trp Glu Tyr Pro Gly Ala Ala
                140                 145                 150

GAT CGT GGC GGC TCT TTT TCT GAC AAG GAC AAA TTC TTA TAC TTA GTG        534
Asp Arg Gly Gly Ser Phe Ser Asp Lys Asp Lys Phe Leu Tyr Leu Val
            155                 160                 165

CAA GAG CTG CGG AGA GCA TTC ATC AGG GTT GGT AAA GGA TGG GAA CTG        582
Gln Glu Leu Arg Arg Ala Phe Ile Arg Val Gly Lys Gly Trp Glu Leu
        170                 175                 180

ACT GCT GCC GTA CCA CTG GCT AAC TTC AGA TTA ATG GAG GGT TAT CAT        630
Thr Ala Ala Val Pro Leu Ala Asn Phe Arg Leu Met Glu Gly Tyr His
    185                 190                 195

GTC CCT GAA CTC TGT CAG GAA TTA GAC GCT ATC CAC GTA ATG TCG TAC        678
Val Pro Glu Leu Cys Gln Glu Leu Asp Ala Ile His Val Met Ser Tyr
200                 205                 210                 215
```

*FIG. 1A.*

```
GAT CTT CGT GGT AAC TGG GCT GGG TTT GCC GAT GTG CAC TCG CCT TTA      726
Asp Leu Arg Gly Asn Trp Ala Gly Phe Ala Asp Val His Ser Pro Leu
            220                 225                 230

TAC AAA CGT CCT CAC GAC CAG TGG GCT TAT GAG AAA CTT AAC GTG AAT      774
Tyr Lys Arg Pro His Asp Gln Trp Ala Tyr Glu Lys Leu Asn Val Asn
            235                 240                 245

GAT GGT CTC CAT CTT TGG GAA GAG AAG GGT TGT CCC TCA AAC AAG CTG      822
Asp Gly Leu His Leu Trp Glu Glu Lys Gly Cys Pro Ser Asn Lys Leu
            250                 255                 260

GTC GTC GGT ATT CCA TTC TAC GGT CGA TCT TTC ACC CTA TCT GCT GGC      870
Val Val Gly Ile Pro Phe Tyr Gly Arg Ser Phe Thr Leu Ser Ala Gly
            265                 270                 275

AAC AAC AAC TAC GGT CTC GGC ACC TTC ATC AAC AAG GAA GCA GGC GGC      918
Asn Asn Asn Tyr Gly Leu Gly Thr Phe Ile Asn Lys Glu Ala Gly Gly
280                 285                 290                 295

GGT GAC CCT GCG CCA TAC ACC AAT GCT ACA GGA TTT TGG GCT TAT TAT      966
Gly Asp Pro Ala Pro Tyr Thr Asn Ala Thr Gly Phe Trp Ala Tyr Tyr
            300                 305                 310

GAG ATC TGT ACA GAA GTA GAC AAG GAT GAC TCC GGC TGG ACG AAG AAA     1014
Glu Ile Cys Thr Glu Val Asp Lys Asp Asp Ser Gly Trp Thr Lys Lys
            315                 320                 325

TGG GAC GAG CAA GGC AAG TGC CCC TAT GCC TAC AAG GGC ACC CAG TGG     1062
Trp Asp Glu Gln Gly Lys Cys Pro Tyr Ala Tyr Lys Gly Thr Gln Trp
            330                 335                 340

GTT GGA TAC GAA GAC CCT CGC AGC GTG GAG ATC AAG ATG AAC TGG ATT     1110
Val Gly Tyr Glu Asp Pro Arg Ser Val Glu Ile Lys Met Asn Trp Ile
            345                 350                 355

AAA CAG AAG GGA TAC CTT GGA GCC ATG ACT TGG GCT ATC GAC ATG GAT     1158
Lys Gln Lys Gly Tyr Leu Gly Ala Met Thr Trp Ala Ile Asp Met Asp
360                 365                 370                 375

GAC TTC AAA GGA CTG TGT GGA GAG AAG AAC CCA TTG ATC AAG ATT CTT     1206
Asp Phe Gln Gly Leu Cys Gly Glu Lys Asn Pro Leu Ile Lys Ile Leu
            380                 385                 390

CAT AAG CAC ATG AGC TCT TAC ACA GTG CCG CCT CCT CAT ACA GAG AAC     1254
His Lys His Met Ser Ser Tyr Thr Val Pro Pro Pro His Thr Glu Asn
            395                 400                 405

ACC ACA CCG ACT CCT GAA TGG GCC CGT CCA CCG TCA ACC CCT TCG GAT     1302
Thr Thr Pro Thr Pro Glu Trp Ala Arg Pro Pro Ser Thr Pro Ser Asp
            410                 415                 420

CCT TCA GAA GGA GAT CCG ATC CCT ACC ACC ACC ACA GCT AAG CCA GCT     1350
Pro Ser Glu Gly Asp Pro Ile Pro Thr Thr Thr Thr Ala Lys Pro Ala
            425                 430                 435

TCT ACC ACC AAA ACG ACC GTG AAG ACT ACT ACC ACT ACC ACA GCA AAA     1398
Ser Thr Thr Lys Thr Thr Val Lys Thr Thr Thr Thr Thr Thr Ala Lys
440                 445                 450                 455
```

*FIG. 1B.*

| | |
|---|---|
| CCA CCT CAG AGC GTC ATT GAT GAA GAG AAT GAT ATT AAT GTG AGG CCT<br>Pro Pro Gln Ser Val Ile Asp Glu Glu Asn Asp Ile Asn Val Arg Pro<br>460 465 470 | 1446 |
| GAA CCA AAA CCC GAA CCT CAA CCA GAG CCT GAA GTT GAA GTG CCT CCT<br>Glu Pro Lys Pro Glu Pro Gln Pro Glu Pro Glu Val Glu Val Pro Pro<br>475 480 485 | 1494 |
| ACT GAA AAT GAA GTC GAT GGT AGC GAA ATC TGC AAC TCA GAC CAA GAT<br>Thr Glu Asn Glu Val Asp Gly Ser Glu Ile Cys Asn Ser Asp Gln Asp<br>490 495 500 | 1542 |
| TAT ATA CCC GAT AAG AAA CAC TGT GAT AAG TAC TGG CGA TGC GTC AAT<br>Tyr Ile Pro Asp Lys Lys His Cys Asp Lys Tyr Trp Arg Cys Val Asn<br>505 510 515 | 1590 |
| GGG GAA GCA ATG CAG TTC TCT TGT CAA CAC GGA ACG GTA TTC AAT GTG<br>Gly Glu Ala Met Gln Phe Ser Cys Gln His Gly Thr Val Phe Asn Val<br>520 525 530 535 | 1638 |
| GAA CTG AAC GTG TGT GAC TGG CCT AGC AAT GCA ACA CGT CGC GAA TGT<br>Glu Leu Asn Val Cys Asp Trp Pro Ser Asn Ala Thr Arg Arg Glu Cys<br>540 545 550 | 1686 |
| CAA CAA CCC TAAAACTATG TTTTATTCAG GAAGTTCAAA TGATACTTCA<br>Gln Gln Pro | 1735 |
| AAATTCGCTC AAATGTCTGA TTTCATGGTC TGTTACACGT TGAAAGTGTT CAATTTGCTA | 1795 |
| TCATTAAAGA ATTCGATTAA TCAGATTCAT GGAAGCGTTA AGATATAGCT AATAAGTTTG | 1855 |
| TGAATATTGT CGTATTTGT TTTAGTTCGA ACATAATACG CCAATGTTTT CTTTAACTAT | 1915 |
| GTAAGGTCTT GATTTATTT TTATTTTTCA TACATAAGTT ACTATTTTAA GCAAATGAGT | 1975 |
| GCTCTCTGCG GACTATAATT GTTCAATACT AATAGGTTGA TTTTCCATTC CAGTGGTATT | 2035 |
| TACCGCCTCG AGTTTTTTTT TAAGACTGCG CATTTTTTAT ATTGTTAAGA CAAAATATTT | 2095 |
| TATTTAAAAT AGTATAGAAT AAATTTGCTC ACTTTAGAAA TAAGCGAATA GAATAAGTTT | 2155 |
| CATACCTACC GAAATTTATT GATGTCGAAT GTGTCCCGTG TTTTTTTTG TAGAATTACG | 2215 |
| TGTTGTATTT GCGCTCTGTT CATAAAATCA TTCAGACAAC TCACGGGAGC AAAAATTCTA | 2275 |
| TTTATTTCTT GGATAAATTT GTTTCGAGTC GGAAGCCAAT TAGCCTGGCT CTTGGCTTCT | 2335 |
| GGGGAATTTA AATGAATTTT CTCGGCACTC TGTGGAAGTG GTCCCGCTTA CTCTTTTAGC | 2395 |
| TTAATTTATT TATTTTTATA ATATAAGTTA ATAAATTATG ATTAAAATTC GGAATTC | 2452 |

*FIG. 1C.*

```
                REGION I                          REGION II
                                                (ACTIVE SITE)

A     (97)  K F M V A V G G W A E G S S K    (136) Y D F D G L D L D W E Y P
B     (98)  K V L L S I G G G A G S Y S L    (142) A V L D G V D F D I E S G
C    (102)  K V L L S L G G A S G S Y L F    (147) A V V D G F D F D I E N N
D    (267)  K I L P S I G G W T L S D P F    (305) K F F D G V D I D W E F P
E     (89)  R I M F S I G G W Y Y S N D L    (132) Y G F D G V D I D W E Y P
F    (335)  K I L Y S F G G W T W S G G F    (374) D V F D G I D L D W E Y P
G    (127)  K V L L S V L G N H Q G A G F    (164) Y G L D G V D F D D E Y A
H    (266)  K I I P S I G G W T L S D P F    (307)       D G V D I D W E F P
I    (441)  K K I P S F G G W D F S T S P    (485) Y N L D G I D L D W E Y P
J     (72)  D V I P S I G G Y S G S K L G    (106) Y G L K A I D V D I E A T
K    (156)  K T I I S V G G W T W S N R F    (194) Y N F D G V D L D W E Y P
L    (258)  K V L I S M G G A N G R I E L    (293) Y G F N G L D I D L E G S
M    (102)  K V M L S L G G G I G N Y S I    (146) A V L D G I D F N I E L G
Consensus   K V L P/L S I G G W T G S - S F        Y V F/L D G I/V D I/F D W E Y P
```

A. Manduca sexta                  This work
B. Cucumis sativa                 Metraux et al. (1989)
C. Saccharomyces cerevisiae       Kuranda and Robbins (1989)
D. Serratia marcescens Chitinase A   Jones et al. (1986)
E. Serratia marcescens Chitinase B   Harpster and Dunsmuir (1989)
F. Streptomyces plicatus          Kuranda and Robbins (1989)
G. Streptomyces plicatus Endo H   Robbins et al. (1984)
H. Vibrio parahemolyticus         Kuranda and Robbins (1989) I. K. latis I.
I. K. latis killer toxin          Stark et al. (1990)
J. Streptomyces erythraeus        Kamei et al. (1989)
K. Bacillus circulans Chitinase A1   Watanabe et al. (1992)
L. Bacillus circulans Chitinase D    Watanabe et al. (1992)
M. Arabidopsis thaliana           Samac et al. (1990)

FIG. 2.

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
        ( A ) LENGTH: 2452 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( v i ) ORIGINAL SOURCE:
        ( A ) ORGANISM: Manduca sexta
        ( D ) DEVELOPMENTAL STAGE: Day 6 fifth instar
        ( F ) TISSUE TYPE: Whole larvae ( v i i ) IMMEDIATE SOURCE:
        ( A ) LIBRARY: Phage Lambda gt11 (Manduca)
        ( B ) CLONE: Clone 201

( i x ) FEATURE:
    ( A ) NAME/KEY: 5'UTR
    ( B ) LOCATION: 1..33
    ( C ) IDENTIFICATION METHOD: experimental
    ( D ) OTHER INFORMATION: /partial
        / evidence= EXPERIMENTAL
        / citation= ([1])

( i x ) FEATURE:
    ( A ) NAME/KEY: 3'UTR
    ( B ) LOCATION: 1696..2452
    ( D ) OTHER INFORMATION: /citation=([1])

( i x ) FEATURE:
    ( A ) NAME/KEY: misc_signal
    ( B ) LOCATION: 34..91

( i x ) FEATURE:
    ( A ) NAME/KEY: misc_feature
    ( B ) LOCATION: 332..367
    ( D ) OTHER INFORMATION: /note= "Conserved Region I"
        / citation= ([1])

( i x ) FEATURE:
    ( A ) NAME/KEY: misc_feature
    ( B ) LOCATION: 439..478
    ( D ) OTHER INFORMATION: /note= "Proposed active site"
        / citation= ([1])

( i x ) FEATURE:
    ( A ) NAME/KEY: CDS
    ( B ) LOCATION: 34..1695

( x ) PUBLICATION INFORMATION:
    ( A ) AUTHORS: Kramer, Karl J.
        Corpuz, Lolita
        Choi, Hee K.
        Muthukrishnan, Subbaratnam
    ( B ) TITLE: SEQUENCE OF A cDNA AND EXPRESSION OF THE GENE
        ENCODING EPIDERMAL AND GUT CHITINASES OF Manduca
        sexta
    ( C ) JOURNAL: Insect Biochem.
    ( D ) VOLUME: 23
    ( E ) ISSUE: 6
    ( F ) PAGES: 691-701
    ( G ) DATE: 6/23-1993
    ( K ) RELEVANT RESIDUES IN SEQ ID NO:1: FROM 1 TO 2452

( x i ) SEQUENCE DESCRIPTION: SEQ ID NO:1:

```
GAATTCCCTC  GCCGACACAC  CGCTACGTTC  AAA  ATG  CGA  GCG  ACA  CTG  GCG  ACG              54
                                         Met  Arg  Ala  Thr  Leu  Ala  Thr
                                          1                    5

TTG  GCT  GTC  CTG  GCC  TTA  GCG  ACG  GCG  GTT  CAA  TCG  GAC  AGC  AGA  GCG         102
Leu  Ala  Val  Leu  Ala  Leu  Ala  Thr  Ala  Val  Gln  Ser  Asp  Ser  Arg  Ala
               10                   15                        20

CGC  ATA  GTA  TGC  TAC  TTC  AGC  AAT  TGG  GCG  GTG  TAT  CGG  CCT  GGT  GTA         150
Arg  Ile  Val  Cys  Tyr  Phe  Ser  Asn  Trp  Ala  Val  Tyr  Arg  Pro  Gly  Val
          25                        30                        35

GGG  CGG  TAC  GGC  ATC  GAG  GAC  ATT  CCA  GTG  GAG  AAG  TGT  ACC  CAC  ATC         198
Gly  Arg  Tyr  Gly  Ile  Glu  Asp  Ile  Pro  Val  Glu  Lys  Cys  Thr  His  Ile
 40                            45                        50                   55

ATT  TAC  TCC  TTC  ATT  GGC  GTC  ACT  GAG  GGC  AAC  AGC  GAA  GTA  CTT  ATC         246
Ile  Tyr  Ser  Phe  Ile  Gly  Val  Thr  Glu  Gly  Asn  Ser  Glu  Val  Leu  Ile
                         60                        65                        70

ATT  GAT  CCT  GAG  TTG  GAT  GTA  GAT  AAG  AAT  GGT  TTC  CGC  AAC  TTT  ACA         294
Ile  Asp  Pro  Glu  Leu  Asp  Val  Asp  Lys  Asn  Gly  Phe  Arg  Asn  Phe  Thr
                    75                        80                        85

TCG  CTT  CGG  TCT  TCG  CAT  CCC  AGC  GTC  AAG  TTC  ATG  GTA  GCG  GTG  GGC         342
Ser  Leu  Arg  Ser  Ser  His  Pro  Ser  Val  Lys  Phe  Met  Val  Ala  Val  Gly
          90                        95                       100

GGC  TGG  GCT  GAA  GGC  AGT  TCG  AAG  TAC  TCT  CAT  ATG  GTT  GCA  CAG  AAG         390
```

| | | | | | | | | | | | | | | | |
|---|---|---|---|---|---|---|---|---|---|---|---|---|---|---|---|
| Gly | Trp | Ala | Glu | Gly | Ser | Ser | Lys | Tyr | Ser | His | Met | Val | Ala | Gln | Lys |
| | 105 | | | | 110 | | | | | 115 | | | | | |

| AGC | ACC | CGC | ATG | TCT | TTT | ATC | AGG | AGC | GTT | GTC | AGT | TTT | CTC | AAG | AAG | 438 |
|---|---|---|---|---|---|---|---|---|---|---|---|---|---|---|---|---|
| Ser | Thr | Arg | Met | Ser | Phe | Ile | Arg | Ser | Val | Val | Ser | Phe | Leu | Lys | Lys | |
| 120 | | | | 125 | | | | | 130 | | | | | | 135 | |

| TAC | GAC | TTC | GAC | GGT | CTA | GAC | CTT | GAT | TGG | GAG | TAC | CCA | GGA | GCC | GCT | 486 |
|---|---|---|---|---|---|---|---|---|---|---|---|---|---|---|---|---|
| Tyr | Asp | Phe | Asp | Gly | Leu | Asp | Leu | Asp | Trp | Glu | Tyr | Pro | Gly | Ala | Ala | |
| | | | | 140 | | | | | 145 | | | | | 150 | | |

| GAT | CGT | GGC | GGC | TCT | TTT | TCT | GAC | AAG | GAC | AAA | TTC | TTA | TAC | TTA | GTG | 534 |
|---|---|---|---|---|---|---|---|---|---|---|---|---|---|---|---|---|
| Asp | Arg | Gly | Gly | Ser | Phe | Ser | Asp | Lys | Asp | Lys | Phe | Leu | Tyr | Leu | Val | |
| | | | 155 | | | | | 160 | | | | | 165 | | | |

| CAA | GAG | CTG | CGG | AGA | GCA | TTC | ATC | AGG | GTT | GGT | AAA | GGA | TGG | GAA | CTG | 582 |
|---|---|---|---|---|---|---|---|---|---|---|---|---|---|---|---|---|
| Gln | Glu | Leu | Arg | Arg | Ala | Phe | Ile | Arg | Val | Gly | Lys | Gly | Trp | Glu | Leu | |
| | 170 | | | | | 175 | | | | 180 | | | | | | |

| ACT | GCT | GCC | GTA | CCA | CTG | GCT | AAC | TTC | AGA | TTA | ATG | GAG | GGT | TAT | CAT | 630 |
|---|---|---|---|---|---|---|---|---|---|---|---|---|---|---|---|---|
| Thr | Ala | Ala | Val | Pro | Leu | Ala | Asn | Phe | Arg | Leu | Met | Glu | Gly | Tyr | His | |
| 185 | | | | | 190 | | | | | | 195 | | | | | |

| GTC | CCT | GAA | CTC | TGT | CAG | GAA | TTA | GAC | GCT | ATC | CAC | GTA | ATG | TCG | TAC | 678 |
|---|---|---|---|---|---|---|---|---|---|---|---|---|---|---|---|---|
| Val | Pro | Glu | Leu | Cys | Gln | Glu | Leu | Asp | Ala | Ile | His | Val | Met | Ser | Tyr | |
| 200 | | | | | 205 | | | | | 210 | | | | | 215 | |

| GAT | CTT | CGT | GGT | AAC | TGG | GCT | GGG | TTT | GCC | GAT | GTG | CAC | TCG | CCT | TTA | 726 |
|---|---|---|---|---|---|---|---|---|---|---|---|---|---|---|---|---|
| Asp | Leu | Arg | Gly | Asn | Trp | Ala | Gly | Phe | Ala | Asp | Val | His | Ser | Pro | Leu | |
| | | | | 220 | | | | 225 | | | | | | 230 | | |

| TAC | AAA | CGT | CCT | CAC | GAC | CAG | TGG | GCT | TAT | GAG | AAA | CTT | AAC | GTG | AAT | 774 |
|---|---|---|---|---|---|---|---|---|---|---|---|---|---|---|---|---|
| Tyr | Lys | Arg | Pro | His | Asp | Gln | Trp | Ala | Tyr | Glu | Lys | Leu | Asn | Val | Asn | |
| | | | 235 | | | | | 240 | | | | | 245 | | | |

| GAT | GGT | CTC | CAT | CTT | TGG | GAA | GAG | AAG | GGT | TGT | CCC | TCA | AAC | AAG | CTG | 822 |
|---|---|---|---|---|---|---|---|---|---|---|---|---|---|---|---|---|
| Asp | Gly | Leu | His | Leu | Trp | Glu | Glu | Lys | Gly | Cys | Pro | Ser | Asn | Lys | Leu | |
| | | 250 | | | | | 255 | | | | | 260 | | | | |

| GTC | GTC | GGT | ATT | CCA | TTC | TAC | GGT | CGA | TCT | TTC | ACC | CTA | TCT | GCT | GGC | 870 |
|---|---|---|---|---|---|---|---|---|---|---|---|---|---|---|---|---|
| Val | Val | Gly | Ile | Pro | Phe | Tyr | Gly | Arg | Ser | Phe | Thr | Leu | Ser | Ala | Gly | |
| | 265 | | | | | 270 | | | | | 275 | | | | | |

| AAC | AAC | AAC | TAC | GGT | CTC | GGC | ACC | TTC | ATC | AAC | AAG | GAA | GCA | GGC | GGC | 918 |
|---|---|---|---|---|---|---|---|---|---|---|---|---|---|---|---|---|
| Asn | Asn | Asn | Tyr | Gly | Leu | Gly | Thr | Phe | Ile | Asn | Lys | Glu | Ala | Gly | Gly | |
| 280 | | | | | 285 | | | | | 290 | | | | | 295 | |

| GGT | GAC | CCT | GCG | CCA | TAC | ACC | AAT | GCT | ACA | GGA | TTT | TGG | GCT | TAT | TAT | 966 |
|---|---|---|---|---|---|---|---|---|---|---|---|---|---|---|---|---|
| Gly | Asp | Pro | Ala | Pro | Tyr | Thr | Asn | Ala | Thr | Gly | Phe | Trp | Ala | Tyr | Tyr | |
| | | | | 300 | | | | | 305 | | | | | 310 | | |

| GAG | ATC | TGT | ACA | GAA | GTA | GAC | AAG | GAT | GAC | TCC | GGC | TGG | ACG | AAG | AAA | 1014 |
|---|---|---|---|---|---|---|---|---|---|---|---|---|---|---|---|---|
| Glu | Ile | Cys | Thr | Glu | Val | Asp | Lys | Asp | Asp | Ser | Gly | Trp | Thr | Lys | Lys | |
| | | | 315 | | | | | 320 | | | | | 325 | | | |

| TGG | GAC | GAG | CAA | GGC | AAG | TGC | CCC | TAT | GCC | TAC | AAG | GGC | ACC | CAG | TGG | 1062 |
|---|---|---|---|---|---|---|---|---|---|---|---|---|---|---|---|---|
| Trp | Asp | Glu | Gln | Gly | Lys | Cys | Pro | Tyr | Ala | Tyr | Lys | Gly | Thr | Gln | Trp | |
| | | 330 | | | | | 335 | | | | | 340 | | | | |

| GTT | GGA | TAC | GAA | GAC | CCT | CGC | AGC | GTG | GAG | ATC | AAG | ATG | AAC | TGG | ATT | 1110 |
|---|---|---|---|---|---|---|---|---|---|---|---|---|---|---|---|---|
| Val | Gly | Tyr | Glu | Asp | Pro | Arg | Ser | Val | Glu | Ile | Lys | Met | Asn | Trp | Ile | |
| | 345 | | | | | 350 | | | | | 355 | | | | | |

| AAA | CAG | AAG | GGA | TAC | CTT | GGA | GCC | ATG | ACT | TGG | GCT | ATC | GAC | ATG | GAT | 1158 |
|---|---|---|---|---|---|---|---|---|---|---|---|---|---|---|---|---|
| Lys | Gln | Lys | Gly | Tyr | Leu | Gly | Ala | Met | Thr | Trp | Ala | Ile | Asp | Met | Asp | |
| 360 | | | | | 365 | | | | | 370 | | | | | 375 | |

| GAC | TTC | CAA | GGA | CTG | TGT | GGA | GAG | AAG | AAC | CCA | TTG | ATC | AAG | ATT | CTT | 1206 |
|---|---|---|---|---|---|---|---|---|---|---|---|---|---|---|---|---|
| Asp | Phe | Gln | Gly | Leu | Cys | Gly | Glu | Lys | Asn | Pro | Leu | Ile | Lys | Ile | Leu | |
| | | | | 380 | | | | | 385 | | | | | 390 | | |

| CAT | AAG | CAC | ATG | AGC | TCT | TAC | ACA | GTG | CCG | CCT | CCT | CAT | ACA | GAG | AAC | 1254 |
|---|---|---|---|---|---|---|---|---|---|---|---|---|---|---|---|---|
| His | Lys | His | Met | Ser | Ser | Tyr | Thr | Val | Pro | Pro | Pro | His | Thr | Glu | Asn | |
| | | | 395 | | | | | 400 | | | | | 405 | | | |

| ACC | ACA | CCG | ACT | CCT | GAA | TGG | GCC | CGT | CCA | CCG | TCA | ACC | CCT | TCG | GAT | 1302 |
|---|---|---|---|---|---|---|---|---|---|---|---|---|---|---|---|---|
| Thr | Thr | Pro | Thr | Pro | Glu | Trp | Ala | Arg | Pro | Pro | Ser | Thr | Pro | Ser | Asp | |
| | | 410 | | | | | 415 | | | | | 420 | | | | |

| CCT | TCA | GAA | GGA | GAT | CCG | ATC | CCT | ACC | ACC | ACC | ACA | GCT | AAG | CCA | GCT | 1350 |

```
                Pro  Ser  Glu  Gly  Asp  Pro  Ile  Pro  Thr  Thr  Thr  Thr  Ala  Lys  Pro  Ala
                     425                     430                      435

TCT  ACC  ACC  AAA  ACG  ACC  GTG  AAG  ACT  ACT  ACC  ACT  ACC  ACA  GCA  AAA                    1398
Ser  Thr  Thr  Lys  Thr  Thr  Val  Lys  Thr  Thr  Thr  Thr  Thr  Thr  Ala  Lys
440                      445                      450                      455

CCA  CCT  CAG  AGC  GTC  ATT  GAT  GAA  GAG  AAT  GAT  ATT  AAT  GTG  AGG  CCT                    1446
Pro  Pro  Gln  Ser  Val  Ile  Asp  Glu  Glu  Asn  Asp  Ile  Asn  Val  Arg  Pro
                         460                      465                      470

GAA  CCA  AAA  CCC  GAA  CCT  CAA  CCA  GAG  CCT  GAA  GTT  GAA  GTG  CCT  CCT                    1494
Glu  Pro  Lys  Pro  Glu  Pro  Gln  Pro  Glu  Pro  Glu  Val  Glu  Val  Pro  Pro
               475                      480                      485

ACT  GAA  AAT  GAA  GTC  GAT  GGT  AGC  GAA  ATC  TGC  AAC  TCA  GAC  CAA  GAT                    1542
Thr  Glu  Asn  Glu  Val  Asp  Gly  Ser  Glu  Ile  Cys  Asn  Ser  Asp  Gln  Asp
          490                      495                      500

TAT  ATA  CCC  GAT  AAG  AAA  CAC  TGT  GAT  AAG  TAC  TGG  CGA  TGC  GTC  AAT                    1590
Tyr  Ile  Pro  Asp  Lys  Lys  His  Cys  Asp  Lys  Tyr  Trp  Arg  Cys  Val  Asn
     505                      510                      515

GGG  GAA  GCA  ATG  CAG  TTC  TCT  TGT  CAA  CAC  GGA  ACG  GTA  TTC  AAT  GTG                    1638
Gly  Glu  Ala  Met  Gln  Phe  Ser  Cys  Gln  His  Gly  Thr  Val  Phe  Asn  Val
520                      525                      530                      535

GAA  CTG  AAC  GTG  TGT  GAC  TGG  CCT  AGC  AAT  GCA  ACA  CGT  CGC  GAA  TGT                    1686
Glu  Leu  Asn  Val  Cys  Asp  Trp  Pro  Ser  Asn  Ala  Thr  Arg  Arg  Glu  Cys
                    540                      545                      550

CAA  CAA  CCC  TAAAACTATG  TTTTATTCAG  GAAGTTCAAA  TGATACTTCA                                      1735
Gln  Gln  Pro

AAATTCGCTC  AAATGTCTGA  TTTCATGGTC  TGTTACACGT  TGAAAGTGTT  CAATTTGCTA                             1795

TCATTAAAGA  ATTCGATTAA  TCAGATTCAT  GGAAGCGTTA  AGATATAGCT  AATAAGTTTG                             1855

TGAATATTGT  CGTATTTTGT  TTTAGTTCGA  ACATAATACG  CCAATGTTTT  CTTTAACTAT                             1915

GTAAGGTCTT  GATTTTATTT  TTATTTTTCA  TACATAAGTT  ACTATTTTAA  GCAAATGAGT                             1975

GCTCTCTGCG  GACTATAATT  GTTCAATACT  AATAGGTTGA  TTTTCCATTC  CAGTGGTATT                             2035

TACCGCCTCG  AGTTTTTTTT  TAAGACTGCG  CATTTTTTAT  ATTGTTAAGA  CAAAATATTT                             2095

TATTTAAAAT  AGTATAGAAT  AAATTTGCTC  ACTTTAGAAA  TAAGCGAATA  GAATAAGTTT                             2155

CATACCTACC  GAAATTTATT  GATGTCGAAT  GTGTCCCGTG  TTTTTTTTTG  TAGAATTACG                             2215

TGTTGTATTT  GCGCTCTGTT  CATAAAATCA  TTCAGACAAC  TCACGGGAGC  AAAAATTCTA                             2275

TTTATTTCTT  GGATAAATTT  GTTTCGAGTC  GGAAGCCAAT  TAGCCTGGCT  CTTGGCTTCT                             2335

GGGGAATTTA  AATGAATTTT  CTCGGCACTC  TGTGGAAGTG  GTCCCGCTTA  CTCTTTTAGC                             2395

TTAATTTATT  TATTTTTATA  ATATAAGTTA  ATAAATTATG  ATTAAAATTC  GGAATTC                                2452
```

( 2 ) INFORMATION FOR SEQ ID NO:2:

( i ) SEQUENCE CHARACTERISTICS:
        ( A ) LENGTH: 554 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

```
Met  Arg  Ala  Thr  Leu  Ala  Thr  Leu  Ala  Val  Leu  Ala  Leu  Ala  Thr  Ala
 1             5                       10                      15

Val  Gln  Ser  Asp  Ser  Arg  Ala  Arg  Ile  Val  Cys  Tyr  Phe  Ser  Asn  Trp
               20                      25                      30

Ala  Val  Tyr  Arg  Pro  Gly  Val  Gly  Arg  Tyr  Gly  Ile  Glu  Asp  Ile  Pro
               35                      40                      45

Val  Glu  Lys  Cys  Thr  His  Ile  Ile  Tyr  Ser  Phe  Ile  Gly  Val  Thr  Glu
```

-continued

|  |  |  |  |  | 50 |  |  |  |  | 55 |  |  |  |  | 60 |  |  |  |  |
|---|---|---|---|---|---|---|---|---|---|---|---|---|---|---|---|---|---|---|---|
| Gly | Asn | Ser | Glu | Val | Leu | Ile | Ile | Asp | Pro | Leu | Asp | Val | Asp | Lys |
| 65 |  |  |  |  | 70 |  |  |  |  | 75 |  |  |  | 80 |
| Asn | Gly | Phe | Arg | Asn | Phe | Thr | Ser | Leu | Arg | Ser | Ser | His | Pro | Ser | Val |
|  |  |  |  | 85 |  |  |  |  | 90 |  |  |  |  | 95 |  |
| Lys | Phe | Met | Val | Ala | Val | Gly | Gly | Trp | Ala | Glu | Gly | Ser | Ser | Lys | Tyr |
|  |  |  | 100 |  |  |  |  | 105 |  |  |  |  | 110 |  |
| Ser | His | Met | Val | Ala | Gln | Lys | Ser | Thr | Arg | Met | Ser | Phe | Ile | Arg | Ser |
|  |  | 115 |  |  |  |  | 120 |  |  |  |  | 125 |  |  |
| Val | Val | Ser | Phe | Leu | Lys | Lys | Tyr | Asp | Phe | Asp | Gly | Leu | Asp | Leu | Asp |
|  | 130 |  |  |  |  | 135 |  |  |  |  | 140 |  |  |  |
| Trp | Glu | Tyr | Pro | Gly | Ala | Ala | Asp | Arg | Gly | Gly | Ser | Phe | Ser | Asp | Lys |
| 145 |  |  |  |  | 150 |  |  |  |  | 155 |  |  |  |  | 160 |
| Asp | Lys | Phe | Leu | Tyr | Leu | Val | Gln | Glu | Leu | Arg | Arg | Ala | Phe | Ile | Arg |
|  |  |  |  | 165 |  |  |  |  | 170 |  |  |  |  | 175 |
| Val | Gly | Lys | Gly | Trp | Glu | Leu | Thr | Ala | Ala | Val | Pro | Leu | Ala | Asn | Phe |
|  |  |  | 180 |  |  |  |  | 185 |  |  |  |  | 190 |  |
| Arg | Leu | Met | Glu | Gly | Tyr | His | Val | Pro | Glu | Leu | Cys | Gln | Glu | Leu | Asp |
|  |  | 195 |  |  |  |  | 200 |  |  |  |  | 205 |  |  |
| Ala | Ile | His | Val | Met | Ser | Tyr | Asp | Leu | Arg | Gly | Asn | Trp | Ala | Gly | Phe |
|  | 210 |  |  |  |  | 215 |  |  |  |  | 220 |  |  |  |
| Ala | Asp | Val | His | Ser | Pro | Leu | Tyr | Lys | Arg | Pro | His | Asp | Gln | Trp | Ala |
| 225 |  |  |  |  | 230 |  |  |  |  | 235 |  |  |  |  | 240 |
| Tyr | Glu | Lys | Leu | Asn | Val | Asn | Asp | Gly | Leu | His | Leu | Trp | Glu | Glu | Lys |
|  |  |  |  | 245 |  |  |  |  | 250 |  |  |  |  | 255 |
| Gly | Cys | Pro | Ser | Asn | Lys | Leu | Val | Val | Gly | Ile | Pro | Phe | Tyr | Gly | Arg |
|  |  |  | 260 |  |  |  |  | 265 |  |  |  |  | 270 |  |
| Ser | Phe | Thr | Leu | Ser | Ala | Gly | Asn | Asn | Tyr | Gly | Leu | Gly | Thr | Phe |
|  |  | 275 |  |  |  |  | 280 |  |  |  |  | 285 |  |  |
| Ile | Asn | Lys | Glu | Ala | Gly | Gly | Gly | Asp | Pro | Ala | Pro | Tyr | Thr | Asn | Ala |
|  | 290 |  |  |  |  | 295 |  |  |  |  | 300 |  |  |  |
| Thr | Gly | Phe | Trp | Ala | Tyr | Tyr | Glu | Ile | Cys | Thr | Glu | Val | Asp | Lys | Asp |
| 305 |  |  |  |  | 310 |  |  |  |  | 315 |  |  |  |  | 320 |
| Asp | Ser | Gly | Trp | Thr | Lys | Lys | Trp | Asp | Glu | Gln | Gly | Lys | Cys | Pro | Tyr |
|  |  |  |  | 325 |  |  |  |  | 330 |  |  |  |  | 335 |
| Ala | Tyr | Lys | Gly | Thr | Gln | Trp | Val | Gly | Tyr | Glu | Asp | Pro | Arg | Ser | Val |
|  |  |  | 340 |  |  |  |  | 345 |  |  |  |  | 350 |  |
| Glu | Ile | Lys | Met | Asn | Trp | Ile | Lys | Gln | Lys | Gly | Tyr | Leu | Gly | Ala | Met |
|  |  | 355 |  |  |  |  | 360 |  |  |  |  | 365 |  |  |
| Thr | Trp | Ala | Ile | Asp | Met | Asp | Asp | Phe | Gln | Gly | Leu | Cys | Gly | Glu | Lys |
|  | 370 |  |  |  |  | 375 |  |  |  |  | 380 |  |  |  |
| Asn | Pro | Leu | Ile | Lys | Ile | Leu | His | Lys | His | Met | Ser | Ser | Tyr | Thr | Val |
| 385 |  |  |  |  | 390 |  |  |  |  | 395 |  |  |  |  | 400 |
| Pro | Pro | Pro | His | Thr | Glu | Asn | Thr | Thr | Pro | Thr | Pro | Glu | Trp | Ala | Arg |
|  |  |  |  | 405 |  |  |  |  | 410 |  |  |  |  | 415 |
| Pro | Pro | Ser | Thr | Pro | Ser | Asp | Pro | Ser | Glu | Gly | Asp | Pro | Ile | Pro | Thr |
|  |  |  | 420 |  |  |  |  | 425 |  |  |  |  | 430 |  |
| Thr | Thr | Thr | Thr | Ala | Lys | Pro | Ala | Ser | Thr | Thr | Lys | Thr | Thr | Val | Lys | Thr |
|  |  | 435 |  |  |  |  | 440 |  |  |  |  | 445 |  |
| Thr | Thr | Thr | Thr | Thr | Ala | Lys | Pro | Pro | Gln | Ser | Val | Ile | Asp | Glu | Glu |
|  |  | 450 |  |  |  |  | 455 |  |  |  |  | 460 |  |  |
| Asn | Asp | Ile | Asn | Val | Arg | Pro | Glu | Pro | Lys | Pro | Glu | Pro | Gln | Pro | Glu |
| 465 |  |  |  |  | 470 |  |  |  |  | 475 |  |  |  |  | 480 |

-continued

| Pro | Glu | Val | Glu | Val 485 | Pro | Pro | Thr | Glu | Asn 490 | Glu | Val | Asp | Gly | Ser 495 | Glu |
| --- | --- | --- | --- | --- | --- | --- | --- | --- | --- | --- | --- | --- | --- | --- | --- |
| Ile | Cys | Asn | Ser 500 | Asp | Gln | Asp | Tyr | Ile 505 | Pro | Asp | Lys | Lys | His 510 | Cys | Asp |
| Lys | Tyr | Trp 515 | Arg | Cys | Val | Asn | Gly 520 | Glu | Ala | Met | Gln | Phe 525 | Ser | Cys | Gln |
| His | Gly 530 | Thr | Val | Phe | Asn | Val 535 | Glu | Leu | Asn | Val | Cys 540 | Asp | Trp | Pro | Ser |
| Asn 545 | Ala | Thr | Arg | Arg | Glu 550 | Cys | Gln | Gln | Pro | | | | | | |

RECOMBINANT CHITINASE AND USE THEREOF AS A BIOCIDE

RELATED APPLICATION

This is a continuation-in-part of application Ser. No. 08/224,987, filed Apr. 8, 1994, now abandoned.

SEQUENCE LISTING

A printed Sequence Listing accompanies this application, and has also been submitted with identical contents in the form of a computer-readable ASCII file on a floppy diskette.

BACKGROUND OF THE INVENTION

1. Field of the Invention

The invention pertains to the field of recombinant deoxyribonucleic acid ("DNA") (or ribonucleic acid "RNA" in the case of a viral genome) host organisms for expressing recombinantly derived proteins. More particularly, the preferred recombinant nucleotides of the invention include a genetic insert coding for insect chitinase, which may be expressed in a variety of organisms. Particularly preferred forms of the invention include a recombinantly derived virus for accelerating the demise of insects, fungi, nematodes and other pests by causing them to express insect chitinase, and a highly insect-resistant recombinant plant that expresses insect chitinase.

2. Description of the Prior Art

Plants utilize chitinase in a variety of defensive mechanisms. By way of example, plant chitinase can degrade fungal cell walls as a defense against fungal pathogens. Additionally, plants secrete increased levels of chitinase in response to insect attack. Grains, in particular, often contain large amounts of chitinases. Unfortunately, while insects contain chitin in the midgut and exoskeleton, the plant chitinases seem to have very little influence upon the feeding activities of plant-eating insects, which have substantially overcome this avenue of plant defense.

Several plant, fungal, and yeast chitinase proteins and/or genes have been reported in the art, e.g., *Cucumis sativa* (Metraux et al., 1989), *Saccharomyces cerevisiae* (Kuranda and Robbins, 1989), *Serratia marcescens* A (Jones et al, 1986), *Serratia marcescens* B (Harpster and Dunsmuir, 1989), *Streptomyces plicatus* (Kuranda and Robbins, 1989), *Streptomyces plicatus* endo H (Robbins et al., 1984), *Vibrio parahemolyticus* (Kuranda and Robbins, 1989), *Streptomyces erythraeus* (Kamei et al., 1989), *Bacillus circulans* A1 (Watanabe et al., 1990), *B. circulans* D (Watanabe et al., 1992) and *Arabidopsis thaliana* (Samac et al., 1990).

The bean chitinase gene was recently inserted into transgenic tobacco (*Nicotiana tabacum*) seedlings, with the effect of producing tobacco plants that are resistant to the fungal pathogen *Rhizoctonia solani*, as reported by Broglie et al., 1991.

SUMMARY OF THE INVENTION

The present invention provides an insect chitinase genetic insert that may be utilized in various recombinant-host expression vectors for the expression of insect chitinase. This gene is particularly useful in recombinantly derived plants and viruses for the purpose of insect control. In general, insect chitinase can be expected to function better against insects than will other types of chitinases. Insect chitinase also may be obtained from chimeric hosts for use as an agent in controlling pests such as fungal pathogens, nematodes and insects.

The invention broadly pertains to a recombinantly derived genetic insert having a nucleotide sequence coding for the host expression of chitinase, as well as corresponding methods and expression vectors that utilize this insert. More specifically, the chitinase genetic insert of the invention is preferably one coding for insect chitinase, and is inserted into a self-replicating vector for the expression of insect chitinase in a host organism. The coding sequence of Sequence ID No. 1, and cDNA sequences encoding chitinase having at least a 50% amino acid sequence homology to the chitinase encoded by Sequence ID No. 1 are particularly preferred. Those skilled in the art will appreciate that such cDNA sequences may contain equivalent codons due to the degeneracy of the translation code, or even minor substitutions and rearrangements of codons, such as may be obtained from site-directed mutagenesis, which may be used to express structurally equivalent amino acid residues. mutagenesis, which may be used to express structurally equivalent amino acid residues.

The chitinase genetic insert may be introduced into a host for expression by a variety of techniques that will be understood by those skilled in the art. These techniques include those for introducing a self-replicating vector for purposes of making a host organism competent for expressing insect chitinase, as well as non-vector methods including the use of biolistic guns, polyethylene glycol-mediated uptake by protoplasts or cells, electroporation, liposome fusion, and microinjection.

One preferred embodiment of the invention pertains to a recombinantly derived viral expression vector including a chitinase coding-region insert for use in controlling pests. The chitinase insert is most preferably one coding for the expression of insect chitinase. The viral expression vector is preferably capable of self-replication in host cells, and may be contained in a viral coating, or in the form of inclusion bodies such as polyhedra for purposes of infecting viral-host insects. Recombinant *baculovirus*, and especially those derived from *Autographa californica*, are particularly preferred for the control of pests such as *Manduca sexta* (tobacco hornworn), *Spodoptera frugiperda* (fall armyworm) and other Lepidoptera. Most preferably, the baculovirus vector of the invention is one designated vAcMNPV.chi, which is a chimeric viral DNA vector including a genetic insert coding for the host expression of insect chitinase. vAcMNPV.chi has been shown to produce an accelerated death rate in a population of insect pests including a 100% demise in the population about twenty-five hours sooner than would be caused by a corresponding wild-type virus which lacks the insect chitinase insert. Virus of the invention may be utilized for pest control according to a method of providing the virus and infecting a population of insects.

Another preferred embodiment of the invention pertains to a recombinantly derived chimeric plant expression vector including an insect chitinase coding-region insert for use in controlling pests. This vector is preferably an *Agrobacterium tumefaciens* (crown gall) vector, and is most preferably inserted into a tobacco (*Nicotina tabacum*) plant. The transgenic plant exhibits a greatly enhanced insect resistance. Other plants may be provided with a similar chimeric insert (i.e., one having an insect chitinase coding region) to exhibit similar insect resistance, for example, corn, bean, wheat, tomato, potato, carrot, rice, and hay plants, as well as ornamental plants.

Plant and virally infected hosts having a chimeric genome including a genetic insert coding for the expression of insect chitinase may be utilized in a method for producing insect chitinase. This method includes the steps of expressing recombinantly derived insect chitinase in the host, and harvesting proteins including insect chitinase-containing proteins either from lysed host cells or from cell growth media having insect chitinase proteins excreted from the host. The method may include a further step of purifying the expressed insect chitinase, and this purification may be conducted by immunoprecipitation or other methods known to those skilled in the art, such as fractionation through an ion- or gel-filtration exchange matrix followed by dialysis of the chitinase-active fractions. The virally infected hosts may include *Spodoptera frugiperda* cell lines or larvae. These method steps will result in proteinaceous products including recombinantly expressed insect chitinase.

BRIEF DESCRIPTION OF THE DRAWINGS

FIG. 1A depicts nucleotide and predicted amino acid sequences of *M. sexta* chitinase from a clone designated as Clone 201;

FIG. 1B is a continuation of the sequence from FIG. 1A;

FIG. 1C is a continuation of the sequence from FIG. 1B;

FIG. 2 depicts a comparison of conserved regions in amino acid sequences of chitinases and related proteins;

DETAILED DESCRIPTION OF THE PREFERRED EMBODIMENT

Figure 3:
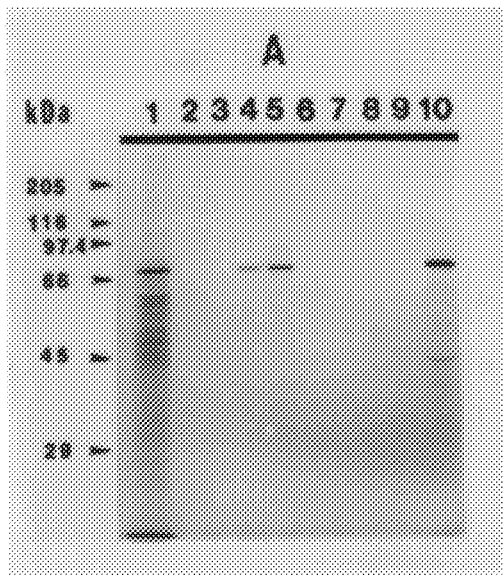
FIG. 3 depicts an autoradiogram obtained from the in vitro translation of *M. sexta* day 6 fifth instar larval mRNA, which was hybrid-selected by *M. sexta* chitinase Clone 10.

Preferred methods and materials for practicing the invention may be utilized according to the following non-limiting examples, by which an insect chitinase gene was isolated from *M. sexta* (tobacco hornworm) and inserted for host expression into baculovirus and tobacco plants, for purposes of insect control.

EXAMPLE 1

INSECTS, TISSUE AND MOLTING FLUID COLLECTION

Insect populations of varying developmental stages were produced and maintained for utilization in the succeeding Examples. Insect rearing, hormone treatments, and tissue collection were conducted according to methods set forth by Corpuz et al. (1991). Samples were obtained from a mixture of day 5 through day 7 fifth instar larvae that had not yet undergone apolysis. This timing was chosen because chitinolytic enzyme activity in *M. sexta* is maximal around the time of apolysis when molting fluid fills the space between the old cuticle and new cuticle being synthesized, as reported by Kramer et al. (1985). Whole larvae, fifth instar integument, fat body, muscle and gut tissues were quick-frozen in liquid nitrogen, stored at −70° C., and thawed directly into 4M guanidine isothiocyanate buffer in preparation for RNA isolation. Molting fluid was collected in a microcapillary tube from day 8 fifth instar larvae through a puncture in the dorsal abdominal horn or a proleg. The fluid was transferred into a plastic microcentrifuge tube containing phenylthio-urea to inhibit phenoloxidase activity, and stored at −20° C.

EXAMPLE 2

INSECT RNA AND DNA ISOLATION

Total RNA was isolated from homogenized tissue of Example 1 by the method of Chirgwin et al. (1979) as modified by Ausubel et al. (1987), for subsequent utilization in the following Examples. Poly(A)$^+$ RNA was isolated from total RNA by oligo(dT)-cellulose column chromatography according to the protocols established by Aviv and Leder (1972). High molecular weight genomic DNA was prepared from day 4 fifth instar larvae as described by Corpuz et al. (1991).

EXAMPLE 3

CHITINASE cDNA LIBRARY CONSTRUCTION

A cDNA library of the *M. sexta* genome was created for purposes of identifying the chitinase gene in subsequent hybridization studies. Poly(A)+ RNA (40 μg) from whole larvae was obtained from Example 2, and used for cDNA synthesis using the standard protocols of Ausubel et al. (1987). After reverse transcription and second strand synthesis, the double-stranded cDNA product was blunt-ended with $T_4$ DNA polymerase and treated with EcoRI methylase to protect EcoRI restriction sites within the cDNA. The cDNA was then ligated to a 150-fold molar excess of EcoRI linkers, digested with EcoRI-digested and size-selected to identify molecules having a length greater than 1600 bp by agarose gel electrophoresis. Following ligation of the cDNA to EcoRI-digested λgll arms, the ligated DNA was packaged into phage particles, which were introduced into *Escherichia coli* Y1090r–(Promega, Madison, Wis.). The cDNA library was amplified on LB agar plates containing 50 μg mL$^{-1}$ ampicillin and 10 mM $MgSO_4$. There were approximately $1.2 \times 10^5$ plaque-forming units in the library with >90% recombinants.

EXAMPLE 4

CHITINASE cDNA LIBRARY SCREENING

The λgll cDNA library of Example 3 was screened using the Lambda-Lift Expression Detection Kit (Bio-Rad Laboratories), in order to identify, for cDNA sequencing analysis, recombinant phage-infected *Eschericia coli* hosts expressing proteins having immunoreactivity with anti-*M. sexta* chitinase antibody. Plating was done at high density ($30-50 \times 10^3$ plaques per 150 mm plate), and the initial screening was carried out with a polyclonal antibody raised against *M. sexta* chitinase, following the methods of Koga et al. (1983b). Sixty-seven positive plaques (from a total of $2 \times 10^5$) were purified by rescreening two or three times with the same antibody probe at a low plating density (200–300 plaques per 100 mm plate). Phage DNA was isolated from positive plaques according to the methods of Ausubel et al. (1987) and subcloned into Bluescript (Stratagene) or M13 vector for further study.

All 67 clones cross-hybridized to one another and one of the larger clones, a 1.8 kb clone designated as Clone 10, was selected for use as a probe in further studies. A later screening of the same cDNA library for larger cross-hybridizing clones resulted in the isolation of Clone 201 with the longest insert (2.45 kb). These two clones and three others were later utilized for a sequencing analysis.

EXAMPLE 5

CHITINASE DNA SEQUENCING

DNA sequencing confirmed that Clones 10 and 201 contained the entire structural coding region for insect chitinase. Five positive clones (of the total 67 positive clones) from Example 4, were selected for cDNA sequence analysis. These clones had cDNA inserts ranging in size from 1.8 kb to 2.5 kb. Clone 10 had a 1.8 kb insert and the longest insert (2.45 kb) was found in Clone 201. All clones with an insert longer than 1.8 kb had an internal EcoRI restriction site. Furthermore, all clones contained an internal BamHI site within the 1.8 kb fragment. This BamHI site was utilized for generating subclones. Inserts from all five clones were subcloned into Bluescript and sequenced by the dideoxy chain termination method (after Sanger et al., 1977) using [$^{35}$S]dATP (after Biggin et al., 1983) and Sequenase version 2.0 (after Tabor and Richardson, 1987). Synthetic primers (complementary to either strand) were used to complete the sequencing. Sequencing reaction products were analyzed on 6% polyacrylamide gels in 7M urea.

FIG. 1 depicts the complete nucleotide sequence and inferred amino acid residue sequence of the insert in Clone 201 (Sequence ID No. 1). The insert DNA is 2452 nucleotides long and contains an internal EcoRI site at position 1804. The sequence for Clone 10 begins at the same position, as does Clone 201, but ends at this EcoRI site. Similarly, the sequences of the three other clones differed from Clone 201 only with respect to the start and end positions of the insert. No sequence heterogeneity was found among the five clones. Clone 201 contains an open reading frame ("ORF") stretching from the AUG codon 34 nucleotides downstream from the 5'-end to position 1695 (see FIG. 1). This ORF of 1662 nucleotides encodes a protein of 554 amino acids and has a molecular weight of 62,210 Da. The 3'-untranslated region of 757 nucleotides is rich in AT and contains several putative polyadenylation signals.

Clone 201, which has an insert of 2,452 nucleotides, appears to be a nearly full length clone (i.e., one having substantially complete 5', coding, and 3' regions) because the transcript detected by this clone is about 2,600 nucleotides long. This size is consistent with the presence of a poly(A)+ tail of 100–200 nucleotides on most eukaryotic mRNAs. The 5'-terminal sequences of at least three different chitinase clones all started at or nearly the same position. Furthermore, the putative translation initiation codon at positions 34–36 (see FIG. 1) is followed by a potential hydrophobic leader peptide expected for a typical secreted protein. This leader peptide suggests synthesis of chitinase on membrane-bound ribosomes.

The inferred amino acid sequence of Clones 10 and 201 included the actual N-terminal sequence of purified chitinase as determined by Edman degradation, which indicated that both clones contained the entire coding region for the chitinase gene. Accordingly, Clone 10, which comprised the shorter fragment, was selected for use in further studies.

Enzymes that hydrolyze β-1,4-N-acetylglucosamine linkages have been classified into three families (Henrissat, 1990). One of these includes the basic plant chitinases, another the exo-cleaving β-N-acetylglucosaminidases, and the third family consists of bacterial, yeast and cucumber chitinases. The *M. sexta* chitinase appears to belong to the latter family of chitinases.

FIG. 2 demonstrates that insect chitinase clearly differs from the basic plant chitinases which lack the conserved regions of other chitinases. The chitinases of FIG. 2 include *M. sexta* (Sequence ID No. 1), *Cucumis sativa* (Metraux et al., 1989), *Saccaromyces cerevisiae* (Kuranda and Robbins, 1989), *Serratia marcescens* A (Jones et al., 1986), *Serratia marcescens* B (Harpster and Dunsmuir, 1989), *Streptomyces plicatus* (Kuranda and Robbins, 1989), *Streptomyces plicatus* endo H (Robbins et al., 1984), *Vibrio parahemolyticus* (Kuranda and Robbins, 1989), *Streptomyces erythraeus* (Kamei et al., 1989), *Bacillus circulans* A1 (Watanabe et al., 1989), *B. circulans* D (Watanabe et al., 1992) and *Arabidopsis thaliana* (Samac et al., 1990). By this comparison, the insect and microbial chitinases are devoid of the cysteine-rich, chitin-binding hevein-like domain found in the class I plant chitinases (Shinshi et al., 1990; Chrispeels and Raikhel, 1991). The protein encoded by Clone 201 has a structure that is made up, in part, of a signal peptide region, chitinase catalytic regions and a threonine/serine-rich region.

EXAMPLE 6

CHITINASE GENE HYBRID SELECTION

Clone 10, of Example 4, which contained only the 1.8 kb fragment, was chosen for hybrid selection experiments because it was shown to contain the entire chitinase coding region by DNA sequencing. The insert DNA from Clone 10 was subcloned into M13mp18 according to the methods of Maniatis et al. (1982). Each of two single-stranded recombinant subclones in opposite orientations (15 μg DNA) was bound to a 2 cm² diazophenyl-thioether cellulose paper. Filters were prehybridized according to the method of Chandra et al. (1985), and hybridized to 1 or 2 mg total RNA from day 6 fifth instar larvae in 50% formamide, 0.4M NaCl, 0.2% SDS, 20 mM Pipes, pH 6.4 and 200 μg mL$^{-1}$ yeast tRNA at 40° C. for 16–18 h, after the methods of Miller et al. (1983). Filters were washed ten times with a buffer containing 10 mM Tris-HCl (pH 7.5), 0.15M NaCl, 1 mM EDTA and 0.2% SDS at 65° C., and further washed three times with the same buffer lacking SDS.

EXAMPLE 7 in vitro CHITINASE TRANSLATION

The filter-bound RNA of Example 6 was eluted from the washed filters in 0.3 mL sterile water containing yeast tRNA, and precipitated by the addition of ethanol. The RNA was solubilized and translated using a rabbit reticulocyte lysate in vitro translation system (Promega) and L-[$^{35}$S] methionine (1000 Ci mmol$^{-1}$; New England Nuclear) as the labeled amino acid. Translation products were analyzed on 8% SDS-polyacrylamide gels according to the methods of Laemmli (1970). The stained gels were treated with Enhance (New England Nuclear), dried and fluorographed using Kodak XAR-5 X-ray film.

FIG. 3 depicts a resultant autoradiogram that was exposed for 16 h. Lane 1 includes total RNA. Lanes 2 and 3 respectively include Clone 10 plus strand hybrid-selected mRNA using 1 and 2 mg of total RNA. Lanes 4 and 5 respectively include Clone 10 minus strand hybrid-selected RNA using 1 and 2 mg of total RNA. Lanes 6, 7, 8 and 10 include proteins immuno-precipitated with chitinase IgG from the following: molting fluid (6); total RNA translation product (7); Clone 10 plus strand hybrid-selected mRNA translation product (8); and Clone 10 minus strand hybrid-selected mRNA translation product (10). Lanes 9 includes Clone 10 minus strand hybrid-selected mRNA translation product immunoprecipitated with preimmune serum. Molecular weight markers (in kDa) are provided on the left. Total RNA translation products included several protein bands as expected (lane 1). With one orientation of the clone, no protein products were detected using the hybrid-selected mRNA translation products (lanes 2 and 3).

EXAMPLE 8

CHITINASE IMMUNUPRECIPITATION

The procedure of Clemens (1984) was used for immunoprecipitation of chitinase immunoreactive protein. Molting fluid (0.1 mL) or translation products were incubated with 0.01 mL preimmune serum and the nonspecific complexes were removed by precipitation with 0.05 mL Protein A—Sepharose beads (Pharmacia). After centrifugation, the supernatant was incubated with 0.02 mL chitinase antiserum or 0.01 ml preimmune serum for 12–16 h at 4° C. and the immune complexes were precipitated by 0.05 mL Protein A—Sepharose beads. Following centrifugation, the pellet was washed six times with immunoprecipitation buffer containing 1 mg ml$^{-1}$ methionine. The washed pellet was heated at 100° C. for 3 minutes in 0.04 mL of SDS-PAGE sample buffer and stored at 20° C. or used immediately for electrophoresis.

The autoradiogram of FIG. 3 depicts, for the opposite orientation clone of lanes 4 and 5, a protein with an apparent molecular weight of 75 kDa. This 75 kDa protein was immunoprecipitated by the chitinase antibody from translations from total RNA and hybrid-selected RNA (lanes 7 and 10). No immunoreactive protein band was found when preimmune serum was used (lanes 9 and 11). The 75 kDa immunoreactive protein has the same size as one of the chitinases isolated from M. sexta pharate pupal molting fluid (Koga et al., 1983).

A discrepancy in molecular mass exists between the size of the hybrid-selected primary translation product and the inferred protein encoded by the open reading frame of Clone 201. The open reading frame of 1,662 nucleotides encodes a protein having an Mr of 62 kDa, a size identical to one of the three chitinases isolated from M. sexta molting fluid (Koga et al., 1983a). However, the major protein in the translation products of mRNA hybrid-selected by the chitinase cDNA clone has an apparent molecular mass of about 75 kDa, a size equal to that of another chitinase present in molting fluid. The relationship between the molting fluid chitinases, which differ in apparent molecular mass, is unknown, but the proteins may be chitinases encoded by separate genes. More probably, the expressed proteins are posttranslationally modified via proteolysis or glycosylation to yield chitinases of different sizes.

EXAMPLE 9

CHITINASE SOUTHERN HYBRIDIZATION

A southern blot analysis indicated the potential presence of more than one insect chitinase gene. A 10 μg sample of genomic DNA from Example 2 was digested with restriction enzymes in separate digestions each containing a 10-fold excess of SmaI, HindIII, EcoRV and BamHI (Promega). The digested DNA was subjected to agarose gel electrophoresis, and transferred onto nitrocellulose. The filters were prehybridized, hybridized, and washed with 0.30M sodium chloride, 0.30M sodium citrate, pH 7.0 (2× SSC) at 65° C., as described by Maniatis et al. (1982). A $^{32}$P-labeled insert DNA probe (based upon Clone 10) had a specific activity of 6×10$^8$ cpm μg$^{-1}$ and was used at 1×10$^6$ cpm mL$^{-1}$ of hybridization solution.

Figure 4:
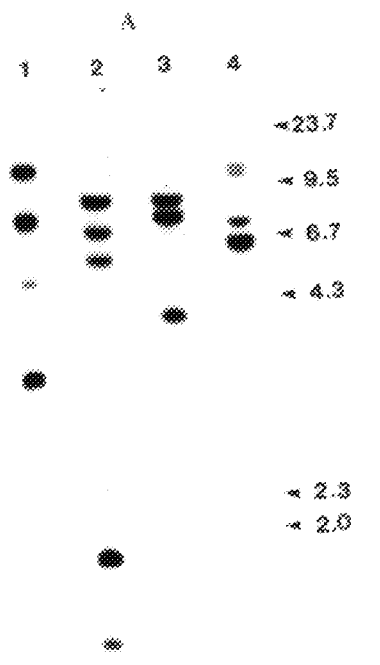
FIG. 4 depicts a southern blot analysis of *M. sexta* genomic DNA using $^{32}$P-labeled insert DNA from Clone 10 as probe, with marker fragments in kilobases (kb) being indicated on the right.

FIG. 4 depicts a southern blot analysis having three to five hybridizing bands with different mobilities that resulted from the four restriction enzyme digests when medium stringency washing conditions (65° C.; 2× SSC) were employed. As depicted, these digests included SmaI (lane 1), HindIII (lane 2), EcoRV (lane 3) and BamHI (lane 4). The results indicate that the Clone 10 cDNA insert has a single site for BamHI, but it has no sites for SmaI, HindIII and EcoRV. The same blot was reprobed with one or the other of the two BamHI fragments derived from the Clone 10 cDNA insert. Of the four bands seen in the BamHI digest (lane 4), only the upper two bands were detected by one BamHI fragment probe, whereas only the lower two bands were detected by the other BamHI fragment probe. These results indicated that two of the four bands in the BamHI digest are due to the presence of internal BamHI sites within the chitinase genes, and suggested the presence of two or more genes encoding chitinases in the M. sexta genome.

EXAMPLE 10

NORTHERN AND RNA SLOT BLOT HYBRIDIZATION

Figure 5:
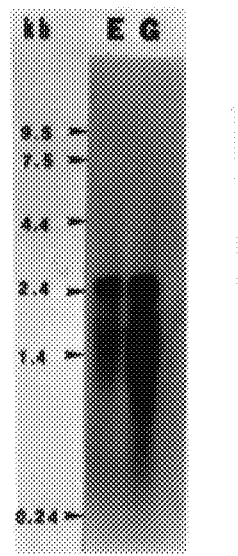
FIG. 5 depicts an autoradiogram of a northern blot of epidermis (E) and gut (G) mRNA (2.5 μg) of *M. sexta* day 6 fifth instar larvae hybridized to $^{32}$P-labeled insert DNA from Clone 10.

It was of interest to determine whether the M. sexta chitinase genes represented by Clone 10 exhibit tissue-specific or time-dependent expression. RNA analysis by Northern and slot blot hybridization was performed and quantitative following the methods of Corpuz et al. (1991). Northern blot analyses of epidermal and gut RNA for day 6 fifth instar *M. sexta* larvae using Clone 10 as the probe detected nucleotide transcripts having a length of about 2600 nucleotides (see FIG. 5).

Figure 6:
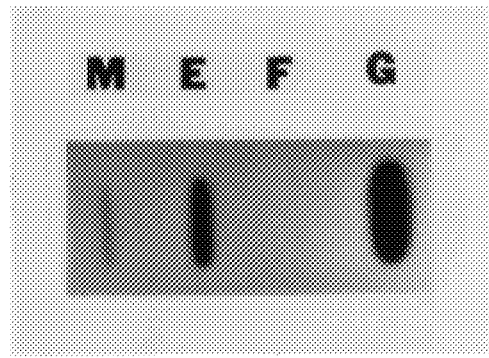
FIG. 6 depicts a slot blot analysis of *M. sexta* chitinase mRNAs in 5 μg total RNA isolated from muscle (M), epidermis (E), fat body (F) and whole gut (G) of day 6 fifth instar larvae.

Total RNA was prepared from muscle, epidermis, fat body and gut tissues of day 6 fifth instar larvae. The amount of chitinase mRNA in each tissue was quantitative by slot blot analysis using 5 μg amounts of RNA (see FIG. 6). On day 6, gut contained the highest concentration of chitinase mRNA on a per microgram RNA basis, followed by epidermis. Muscle contained a very low amount of chitinase mRNA, whereas fat body contained none. These results indicated that on day 6 of the fifth instar, gut and epidermis are the major tissues that express chitinase genes.

Figure 7:
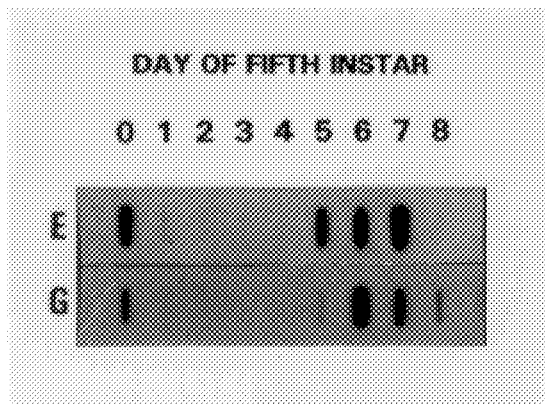
FIG. 7 depicts a slot blot analysis of *M. sexta* chitinase mRNAs in 2.5 μg of total RNA from day 0 through day 8 fifth instar larvae of (A) epidermis and (B) gut, with numbers indicating the day of fifth instar.

Changes in the levels of chitinase transcripts in epidermal and gut tissues throughout development of fifth instar larvae were also determined by slot blot analyses. For this purpose, duplicate blots of total RNA from day 0 through day 8 fifth instar larvae were probed with $^{32}$P-labeled insert DNA from Clone 10. FIG. 7 shows that chitinase mRNA was present in relatively high levels in epidermis on day 0, but it disappeared rapidly and was undetected on day 1 through day 4 of fifth instar. Chitinase mRNA reappeared on day 5 and peaked on day 7 after which a sharp decline occurred. In the gut, it was detected primarily on day 6 with lower levels present on days 0, 7 and 8. Thus, there was both tissue and development-specific expression of chitinase genes in *M. sexta* during the larval-pupal transformation. Chitinase gene expression in epidermis occurred one day earlier and was somewhat greater than that in the gut.

EXAMPLE 11

INFECTION OF HOST CELLS WITH A BACULOVIRUS

Commercially available *Spodoptera frugiperda* (army hornworm) cell lines were propagated and maintained in an appropriate growth medium for subsequent infection with a baculovirus. Cell lines SF9 and SF21 (from GIBCO BRL of Gaithersburg, Md.) were propagated at 28° C. in SF-900ll (GIBCO BRL) serum-free insect cell culture media. The *S. frugiperda* Hi-5 cell line (from JRH Biosciences of Lenexa, Kans.) was propagated in EXCELL-400 (JRH) serum-free medium containing L-glutamine. Wild-type *Autographa californica* nuclear polyhedrosis virus (vAcMNPV.wt) was obtained from GIBCO BRL. Cell culture techniques were as described by Summers and Smith (1987). Viral infection of insect cells was carried out using the BaculoGold Transfection Kit from PharMingen (San Diego, Calif.).

EXAMPLE 12

CONSTRUCTION OF RECOMBINANT BACULOVIRUS

Recombinant DNA techniques were employed to generate a self-replicating baculovirus vector containing an insert coding for the expression of insect chitinase in a host cell. The *E. coli* transfer vector pVL1393 was purchased from Invitrogen of San Diego, Calif. The 9.2 kb *E. coli* transfer vector pVL1393 contained the promoter for the polyhedron gene followed by a polylinker with a unique restriction site for EcoRI. The 1.8 kb EcoRI fragment from *M. sexta* chitinase Clone 201 (Sequence ID No. 1) was inserted at the EcoRI site of pVL1393 in the correct orientation to produce the transfer plasmid pVL1393.chi. All DNA manipulations were conducted according to the standard procedures of Maniatis et al. (1992). Restriction enzyme analysis (with BamHI) was performed according to conventional protocols, in order to confirm the structure of the construct.

One-half pg of linearized BaculoGold virus DNA was mixed with 2 μg of the transfer plasmid pVL1393.chi and used for transfection of 3×10$^6$ SF9 cells following the procedure described in Pharmingen catalog no. 21000K. The resultant recombinant baculovirus vAcMNPV.chi was amplified by culturing it in SF9 cells, and the medium containing the recombinant virus was used for infecting the cells. Almost 100% recombinants were produced using the BaculoGold Transfection Kit. vAcMNPV.chi was occlusion negative and contained an active ecdysteroid glucosyl transferase (egt$^+$) gene (Eldridge et al., 1992). The occlusion negative nature of vAcMNPV.chi indicated successful cloning with an insert that, as planned, disrupted the polyhedron gene, thereby resulting in the subsequent host expression of a budded virus. vAcMNPV.wt (which was occlusion positive, egt$^+$ and chi$^-$) was used as the control virus for subsequent in vivo comparison with the recombinant virus. Baculovirus vAcMNPV.chi has been deposited in the American Type Culture Collection, Rockville, Md. and has been accorded Accession No. 97248.

EXAMPLE 13

WESTERN BLOT ANALYSIS OF RECOMBINANT VIRAL CHITINASE

A western blot analysis was conducted to confirm the host insect cell expression of recombinantly derived *M. sexta* chitinase after infection with the budded virus of Example 12 (vAcMNPV.chi). One million cells in SF-900ll media (SF9 and SF21 cells) or EXCELL-400 media (Hi-5 cells) were seeded on a 35 mm tissue culture dish in a final volume of 2 mL for 30 min. to 1 h at 28° C. The medium was then removed and cells were infected at a multiplicity of infection ("MOI") of 20 plaque forming units (PFU) per cell with either vAcMNPV.wt or vAcMNPV.chi for one hour at room temperature. The viral inoculum was removed, and cells were incubated with 2 mL cell culture medium at 28° C. Two days after infection, medium from the dish was collected, centrifuged at 12,000 g for five min. to remove floating cells, and an aliquot of the supernatant was subjected to 3–17% gradient sodium dodecyl sulfate polyacrylamide gel electrophoresis (SDS-PAGE, Jule Inc. Biotechnologies, New Haven, Conn.), according to the methods of Laemmli (1970). Proteins were transferred to a PVDF membrane with a Semi-Dry Electroblotter (Integrated Separation Systems) using the manufacturer's instructions. The membranes were blocked with 2.5% gelatin and then processed as described by Winston et al., 1987. A polyclonal antibody to chitinase from molting fluid of fifth instar *M. sexta* larvae (Koga et al., 1983a) was used to detect chitinase-related proteins in immunoblot analysis. Cells were suspended in a buffer including 20 mM Tris and 2mM EDTA, and lysed either by sonication for activity assay or by suspension in SDS-gel loading buffer (4% SDS, 125 mM Tris-HCl pH 6.7, 30% (v/v) glycerol, 0.002% w/v bromophenol blue and 2% (v/v) β-mercaptoethanol).

Western blot analysis was also performed upon 10 μL of hemolymph samples collected from recombinant, wild-type virus-infected or uninfected larvae six days after infection using the above conditions for gel runs.

Figure 8:
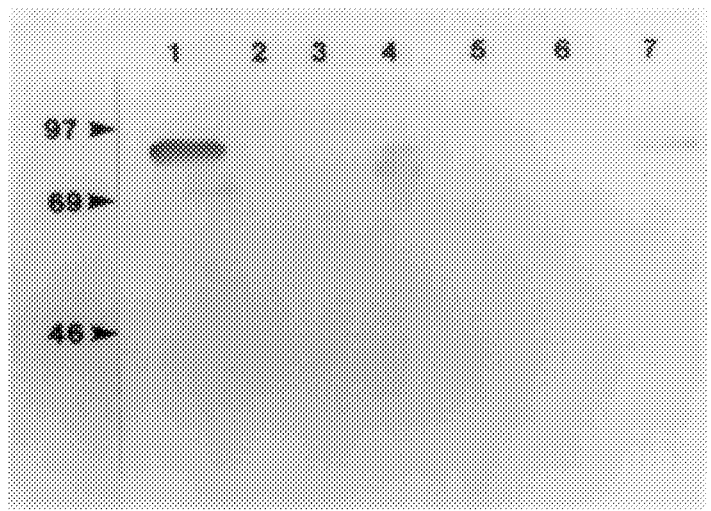
FIG. 8 depicts a western blot analysis demonstrating expression of *M. sexta* chitinase in baculovirus-infected SF9 cells.

FIG. 8 depicts an exemplary western blot analysis (SDS-PAGE followed by immunoblot with antibody to *M. sexta* chitinase) for 60 μg of medium proteins and 25 μg of cell lysate proteins. Molecular size markers are given in kDa. Lane 1 includes 1 μL molting fluid from fifth instar *M. sexta* larvae. Lane 2 includes cell lysate from uninfected larvae. Lane 3 includes wild-type virus-infected cell lysate. Lane 4 includes recombinant virus-infected cell lysate. Lane 5 includes medium from an uninfected sample. Lane 6 includes medium from a wild-type sample. Lane 7 includes medium from a recombinant sample.

The results of FIG. 8 indicate that an immunoreactive protein of about 85 kDa in size was present in both the lysate and medium of cells infected with the recombinant virus (FIG. 8, lanes 4 and 7, respectively). This band was absent in medium and lysate from control cells and wild-type virus infected cells (lanes 2, 3, 5 and 6). The size of the recombinant protein in the medium was the same as the chitinase present in molting fluid of fifth instar *M. sexta* larvae (FIG. 8, lane 1). The cell lysates also contained a slightly smaller protein, which was more abundant than the 85 kDa protein; however, most of the immunoreactive chitinase was found in the medium as the slower migrating 85 kDa protein. Thus, recombinant chitinases were present not only in the cells, but were also secreted into the medium.

EXAMPLE 14

CHITINASE ACTIVITY ASSAY

An activity gel study confirmed that host insect cells infected with the budded virus of Example 12 (vAcMNPV.chi) expressed biologically active *M. sexta* chitinase. Samples were subjected to electrophoresis in a 7.5% native polyacrylamide minigel, after the methods of Blackshear (1984). After electrophoresis the gel was overlaid with a 7.5% polyacrylamide gel containing 0.1% glycol chitin as a substrate and incubated at 37° C. for 1.5 hours, according to the procedure of Trudel & Asselin (1989). Chitinase bands were detected by the absence of staining with calcofluor when viewed under ultraviolet light.

Quantitation of chitinase activity was done using a colorimetric assay with carboxymethyl Remazol Brilliant Violet (CM-Chitin-RBV) as the substrate (Loewe Biochemica, Nordring, Germany). Samples were diluted with water to 0.4 mL and incubated at 37° C. with 0.2 mL of 0.2M phosphate-citrate buffer pH 7.5 and 0.2 mL of CM-Chitin-RBV for one or two hours. The reaction was stopped with 0.2 mL of 2N HCl and the samples were cooled in ice for 15 min. After the samples were centrifuged at 12,000 g for five min, the absorbance at 550 nm of the supernatants were determined.

Figure 9:
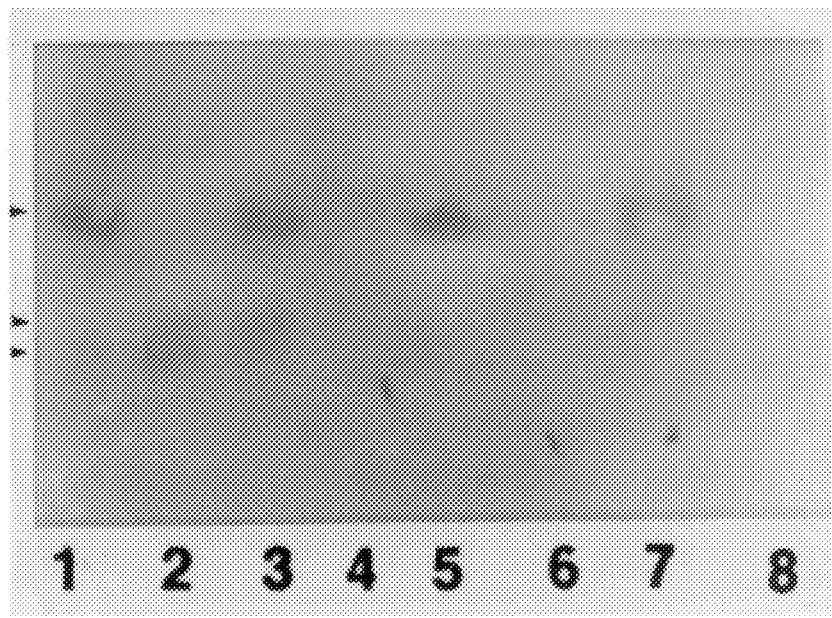
FIG. 9 depicts an activity gel demonstrating chitinase enzymatic activity in baculovirus-infected SF9 cells.

Aliquots of the same samples used for immunoblot analysis in Example 13 were utilized for chitinase activity assays using glycol chitin as the substrate (Trudel and Asselin, 1989) following native gel electrophoresis (see FIG. 9). The lysate and medium from recombinant virus infected cells exhibited a band with chitinase activity having the same mobility (0.52) as the chitinase present in molting fluid (lanes 3 and 7). This band was absent from lysates and media from control and wild-type virus infected cells (lanes 2, 4 and 6). The two higher mobility bands (0.67 and 0.71 respectively) with chitinase activity were also observed in both the wild-type and recombinant virus infected SF9 cells but these other proteins were apparently chitinases endogenous to the virus. The viral chitinases did not cross-react with the *M. sexta* chitinase antibody. They were not detected in molting fluid (lanes 1 and 5). The viral chitinase must be immunologically unrelated to *M. sexta* chitinase, because no cross-reactive material was detected in wild-type virus infected cells by the *M. sexta* chitinase antibody.

FIG. 9 depicts a chitinase activity gel for samples containing 25 μg of protein. The position of chitinase is indicated by an arrow. Lanes 1 and 5 include 1 μL of molting fluid. Lane 2 includes wild-type cell lysate. Lane 3 includes recombinant cell lysate. Lane 4 includes uninfected cell lysate. Lane 6 includes medium from a wild-type sample. Lane 7 includes medium from a recombinant sample. Lane 8 includes medium from an uninfected sample.

EXAMPLE 15

TIME COURSE OF HOST EXPRESSION OF RECOMBINANT CHITINASE

Figure 10:
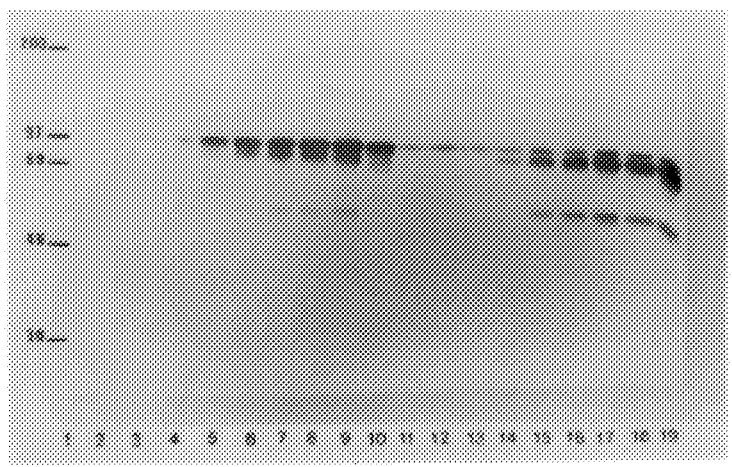
FIG. 10 depicts a western blot analysis demonstrating the time course of expression of *M. sexta* chitinase in SF9 cells.

A comparative study was performed to ascertain the time course for *M. sexta* chitinase expression in SF9 cells. SF9 cells infected with the vAcMNPV.chi virus were harvested at various times, and subjected to a western blot analysis to determine the relative levels of *M. sexta* chitinase expression. These cells expressed *M. sexta* chitinase as early as eight hours post infection (FIG. 10, lane 11). The most abundant chitinase from the medium was about 85 kDa in size, and exhibited a dramatic increase in expression level from 32 to 40 hours post-infection and continued to increase at later time points. With increasing time after infection, an immunoreactive protein of apparent molecular weight of 52 kDa was also detected. Whereas the most abundant form of recombinant chitinase in the medium had a molecular weight of 85 kDa, and appeared after eight hours post-infection, this protein appeared to have reached a steady-state level in the cells. The 52 kDa protein appeared about 40 hours post-infection and increased in amount with time thereafter (FIG. 10, lanes 11–19 and FIG. 8, lane 4). The major protein in the cell lysate was approximately 80 kDa in size, appeared about 32 hours post-infection and continued to increase with time thereafter.

In more detail, FIG. 10 is a western blot analysis demonstrating the time course of expression of *M. sexta* chitinase in SF9 cells. Lanes 1–9 include media from infected cells harvested at 8, 16, 24, 32, 40, 48, 56, 64 and 72 hours respectively. Lanes 11–19 include cell lysate from infected cells collected at 8, 16, 24, 32, 40, 48, 56, 64 and 72 hours respectively. Lane 10 includes molting fluid from fifth instar *M. sexta* larvae.

In a further analysis, an in vivo comparative study was conducted to determine the relative effect of viral infection upon host larvae expression of *M. sexta* chitinase. *S. frugiperda* larvae were a gift from Dr. Thomas Coudron (Biocontrol Laboratory, ARS-USDA, Columbia, Mo.). *S. frugiperda* fourth instar larvae were injected with 2×10$^5$ PFU of either budded vAcMNPV.chi or vAcMNPV.wt. Hemolymph was collected from the infected and control larvae at 24 h intervals post-infection and subjected to either western blot analysis (FIG. 11) or chitinase activity assay (FIG. 12).

Figure 11:
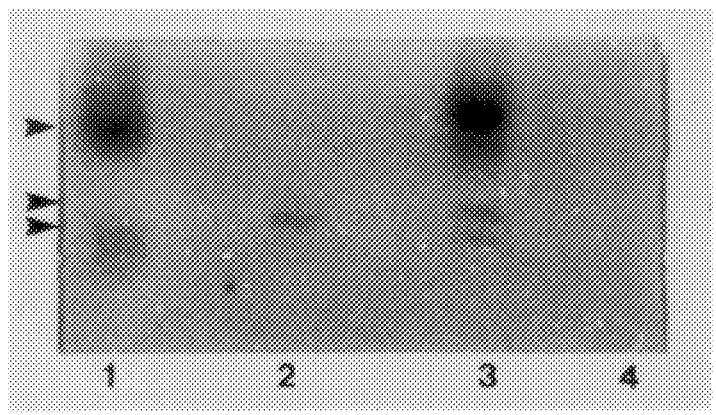
FIG. 11 depicts a western blot demonstrating the time course of expression of *M. sexta* chitinase in hemolymph of fourth instar *Spodoptera frugiperda* larvae infected with vAcMNPV.wt or vAcMNPV.chi.

Recombinant protein was detected in the hemolymph of *S. frugiperda* larvae infected with the recombinant virus, as early as 24 h after infection (FIG. 11, lane 4) and continued to increase up to 72 h after infection (FIG. 11, lanes 6, 8). The mobility of the recombinant protein was identical to that of chitinase present in molting fluid of *M. sexta* larvae (lane 11). Hemo-lymph from the control larvae (lanes 3 and 10) and wild-type virus-infected larvae (lanes 2, 5, 7 and 9) was deficient in immunoreactive chitinase.

Figure 12:
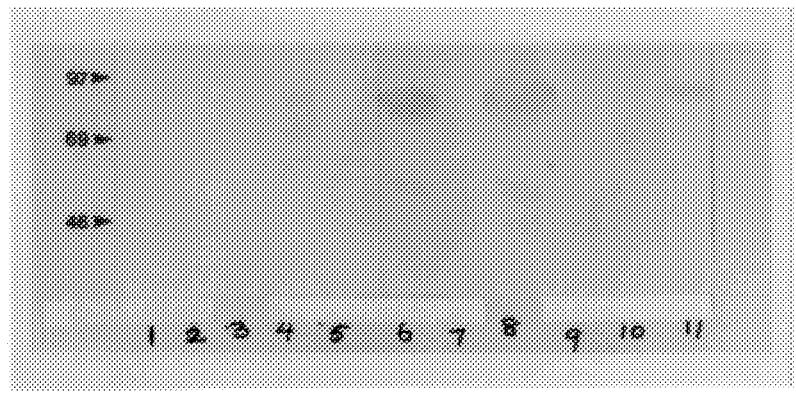
FIG. 12 depicts an activity gel demonstrating chitinase activity in hemolymph of fourth instar *M. sexta* larvae infected with vAcMNPV.wt or vAcMNPV.chi.

Hemolymph from larvae bled three days post-infection was used for chitinase activity assay using glycol chitin as the substrate (FIG. 12). Once again, the mobility of the band with chitinase activity in both molting fluid and recombinant virus infected larvae appeared to be identical (0.382). As with the activity assay using cell culture extracts (see FIG. 9), a higher mobility band (0.58) with chitinase activity was observed in hemolymph from both the wild-type and recombinant virus-infected larvae (lanes 2 and 3, respectively). This protein, as predicted earlier, was probably a viral chitinase.

In FIG. 11, lanes 1–3 respectively include hemolymph taken 0 days after infection with vAcMNPV.chi (lane 1); vAcMNPV.wt (lane 2); 3 uninfected cell (lane 3). Lanes 4–5 respectively include hemolymph taken 1 day after infection with vAcMNPV.chi (lane 4) and vAcMNPV.wt (lane 5). Lanes 6–7 include hemolymph taken two days after infection with vAcMNPV.chi (lane 6) or vAcMNPV.wt (lane 7). Lanes 8–10 respectively include hemolymph taken three days after infection with vAcMNPV.chi (lane 8), vAcMNPV.wt (lane 9) or uninfected cells (lane 10). Lane 11 includes 2 µL molting fluid from fifth instar *M. sexta* larvae.

In FIG. 12, lane 1 includes molting fluid from fifth instar *M. sexta* larvae. Lane 2 includes hemolymph taken three days after infection with vAcMNPV.wt. Lane 3 includes hemolymph taken three days after infection with vAcMNPV.chi.

EXAMPLE 16

CHITINASE GLYCOSYLATION STUDIES

A glycosylation study confirmed that both normal and recombinantly expressed insect chitinase undergoes normal cellular glycosylation and, consequently, glycosylated immunoreactive chitinases having a common genetic origin may be found with varying molecular weights. The chitinase glycosylation pathway is also implicated in the transmembrane secretion of insect chitinase from the cytoplasm and into the growth media. Tunicamycin obtained from Sigma Chemical of St. Louis, Mo. was added to the cells 15 hours after infection with the virus at a concentration of 5 µg mL$^{-1}$. The cells were incubated for an additional 33 h after which the media and cells were separated and analyzed for chitinase using 3–17% gradient SDS-PAGE followed by immunoblot analysis.

Carbohydrate analysis of chitinase from molting fluid of fifth instar *M. sexta* larvae was done by subjecting 10 µL of molting fluid to 3–17% gradient SDS-PAGE followed by transfer onto a PVDF membrane. After transfer, the membrane was stained with Coomassie brilliant blue R-250 (0.4% in 10% acetic acid) for five min., followed by destaining in 80% methanol for five min. The band corresponding to chitinase was identified by treating a duplicate blot with the antibody to chitinase for 3 h. Bound antibody was detected with horseradish peroxidase-conjugated anti-rabbit IgG. The band corresponding to chitinase was cut out from the Coomassie blue stained membrane and carbohydrate composition was determined at the Experimental Station Chemical Laboratories, University of Missouri-Columbia. Samples were hydrolyzed to liberate carbohydrate moieties and sugars were reduced and derivatized to alditol or hexosaminitol acetates which were separated by gas-liquid chromatography and quantified by mass spectrometry (applying methods of Mawhinney et al., 1980; Mawhinney, 1986; and Tilley et al., 1993).

Carbohydrate analysis of *M. sexta* chitinase expressed in recombinant baculovirus (vAcMNPV.chi) infected Hi-5 cells was also done. One million Hi-5 cells in EXCELL-400 media, seeded on a 35 mm tissue culture dish was infected with vAcMNPV.chi at a multiplicity of infection of 20 PFU per cell. The viral inoculum was removed after an hour and the cells were incubated with 2 mL culture medium at 28° C. for two days after which the medium containing the expressed chitinase was collected and centrifuged to remove floating cells. One mL of the media was subjected to trichloroacetic acid precipitation to concentrate the protein, the protein wa suspended in sample buffer and subjected to 3%–17% gradient SDS-PAGE. After the run, the gel was stained with Coomassie brilliant blue R-250 (0.2% in 20% methanol, 10% acetic acid). The band corresponding to *M. sexta* chitinase was cut out and carbohydrate composition was determined as above.

The multiplicity of immunoreactive chitinases in cell lysates and media (FIG. 10) and the difference between the molecular weights of the recombinant enzyme (85 kDa) and the conceptual protein predicted from the nucleic acid sequence (62 kDa) called for an investigation of whether this heterogeneity was due to glycosylation.

Figure 13:
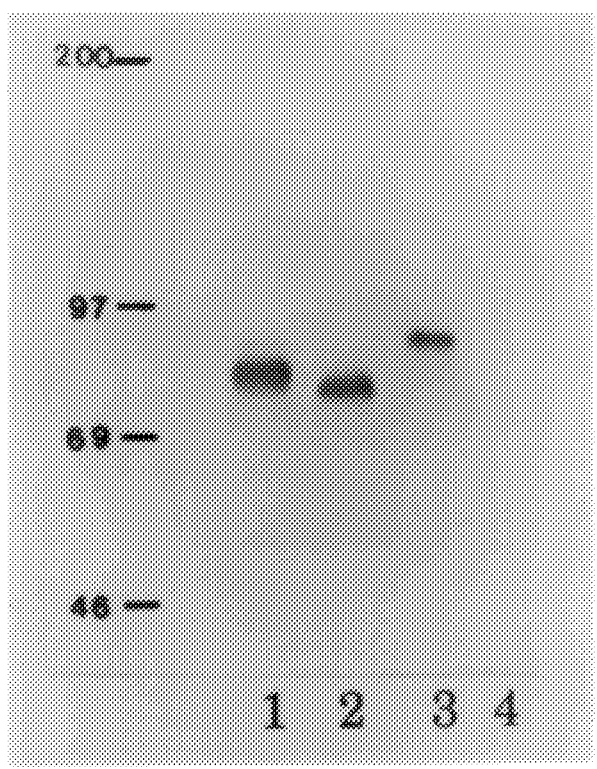
FIG. 13 depicts a western blot analysis demonstrating the effects of tunicamycin on the expression of *M. sexta* chitinase.

FIG. 13 is a western blot that demonstrates the effects of tunicamycin on expression of *M. sexta* chitinase by monitoring expression of chitinase in recombinant virus-infected SF9 cells from 15 hours post-infection to 48 hours post-infection in the presence or absence of tunicamycin, which is an inhibitor of N-linked glycosylation of protein. Lane 1 includes (−) tunicamycin treated cell lysate. Lane 2 includes (+) tunicamycin treated cell lysate. Lane 3 includes (−) tunicamycin treated medium. Lane 4 includes (+) tunicamycin treated medium.

In the absence of tunicamycin, chitinase was released into the medium as a 85 kDa protein (FIG. 13, lane 3). Tunicamycin inhibited the secretion of chitinase into the medium (FIG. 13, lane 4). In cells not treated with tunicamycin, the antibody to *M. sexta* chitinase cross-reacted with a protein of approximately 80 kDa. A trace amount of the 85 kDa protein was also detailed (FIG. 13, lane 1). Cells treated with tunicamycin showed the existence of a immunoreactive protein with an apparent molecular weight of only 75 kDa (FIG. 13, lane 2). The larger proteins from the cells not treated with tunicamycin are apparently glycosylated forms of chitinase. Glycosylation appears to be required for secretion of the protein into the medium, because in the presence of tunicamycin no cross-reactive material was detected in the medium and the 80 kDa chitinase was found only in cell extracts.

Table 1 shows the carbohydrate content of chitinases isolated from molting fluid and the cell culture medium. The carbohydrate composition was similar between the two chitinases, accounting for 20–30% of the mass of enzymes.

EXAMPLE 17

CHITINASE YIELD FROM INFECTED CELL LINES

Figure 14:
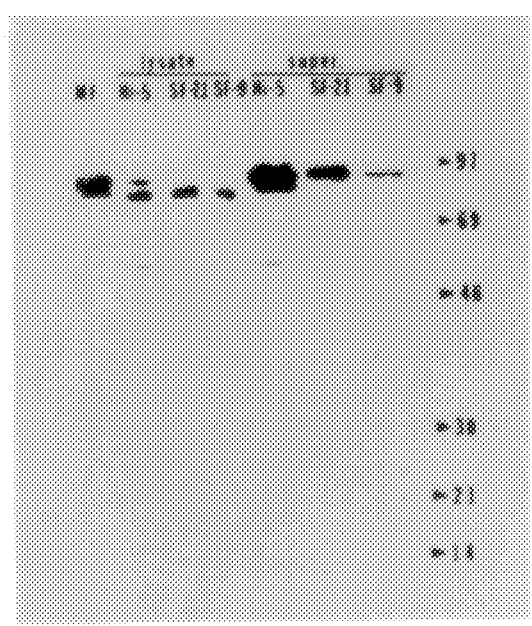
FIG. 14 depicts a western blot analysis demonstrating the expression of *M. sexta* chitinase in virally infected cell lines.
Figure 15:
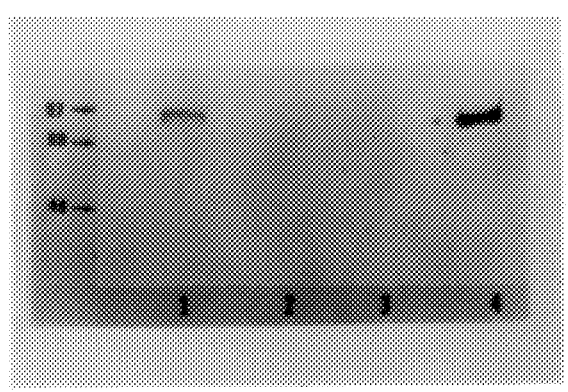
FIG. 15 depicts a western blot analysis of hemolymph of fourth instar *M. sexta* larvae virally infected with vAcMNPV.wt or vAcMNPV.chi.
Figure 16:
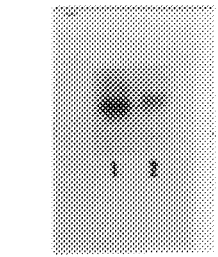
FIG. 16 is an activity gel demonstrating chitinase activity in hemolymph of fourth instar *M. sexta* larvae virally infected with vAcMNPV.wt or vAcMNPV.chi.
Figure 17:
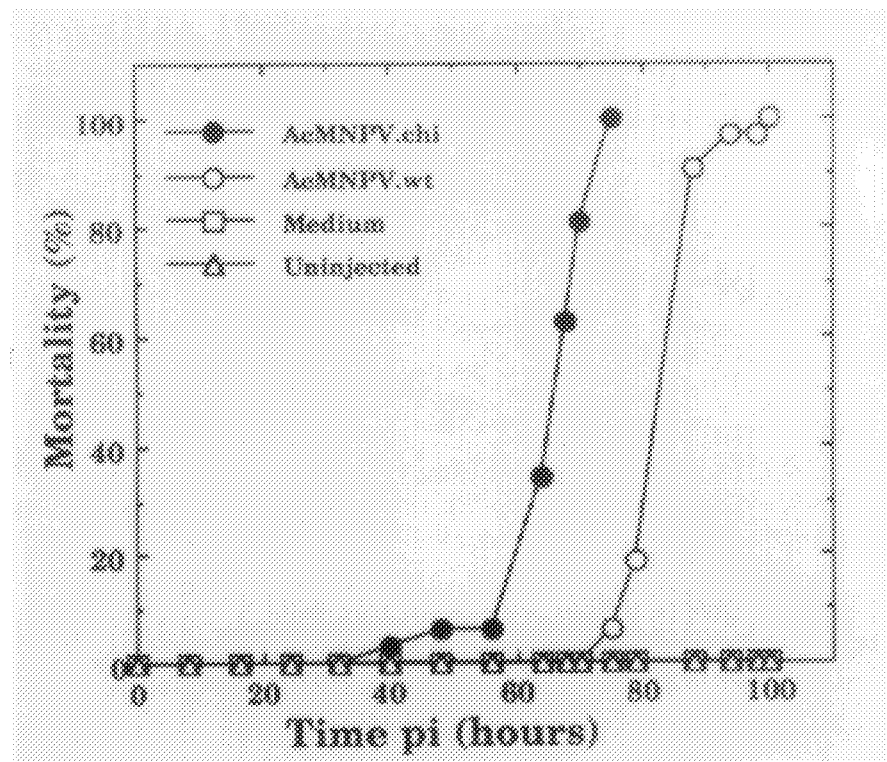
FIG. 17 is a cartesian plot of data comparing the mortality, over time, of fourth instar *S. frugiperda* larvae after infection with a recombinant baculovirus versus a wild-type baculovirus infection.

A comparative analysis of the expression of recombinant chitinase in SF9, SF21 and *Trichoplusia ni* Hi-5 cell lines revealed that the relative yield was in the order Hi-5>SF21>SF9 (FIG. 14). The level of chitinase activity in media from vAcMNPV.wt, vAcMNPV.chi or mock infected SF9, SF21 and Hi-5 cell lines was also determined (Table 2). The activity in recombinant virus infected cell lines was in the order Hi-5>SF21>SF9. Control samples including media from vAcMNPV.wt or mock-infected cells exhibited no activity.

In support of these observations, FIG. 14 is a western blot analysis demonstrating the expression of *M. sexta* chitinase in virally infected cell lines. Lane 1 includes molting fluid. Lane 2 includes Hi-5 cell lysates. Lane 3 includes SF21 cell lysates. Lane 4 includes SF9 cell lysates. Lane 5 includes medium from a Hi-5 sample. Lane 6 includes medium from a SF21 sample. Lane 7 includes medium from a SF9 sample.

EXAMPLE 18

CHITINASE N-TERMINAL SEQUENCING

Protein was subjected to SDS-PAGE, electroblotted onto PVDF membrane, stained with Coomassie brilliant blue, cut out and subjected to automated Edman degradation using an Applied Biosystems sequencer (Matsudaira, 1987; Tempst and Riviere, 1989) at the Biotechnology Micro-chemical Core Facility, Kansas State University, Manhattan.

Analysis of the amino acid sequence of chitinases isolated from molting fluid and from baculovirus infected Hi-5 cells revealed that the first 6 residues of the N-terminal sequences Asp-Ser-Arg-Ala-Arg-Ile were identical (positions 20–25 of Sequence ID No. 2).

EXAMPLE 19

INSECT BIOASSAYS USING THE RECOMBINANT VIRUS

Insect bioassays were conducted to determine the effect of infecting larvae with vAcMNPV.chi in comparison to vAc-MNPV.wt. The mortality of S. frugiperda larvae was determined as a function of time to establish whether inclusion of the chitinase gene into the AcMNPV genome would enhance the insecticidal activity of the baculovirus.

Twenty five to thirty S. frugiperda larvae, approximately in the late fourth or early fifth instar, were injected with $2\times10^5$ pfu's of vAcMNPV.wt or vAcMNPV.chi, following the methods of Eldridge et al. (1992). Controls were either uninjected larvae or larvae injected with media. Infected and control insects were reared individually on artificial diet at 28° C. on a 14:10 h light:dark cycle. Mortality of insects was recorded every 8 h following infection and $LT_{50}$ analyzed by probit analysis after Daum (1970).

Hemolymph was collected from larvae six days after infection and monitored for the presence of recombinant protein using an antibody to *M. sexta* chitinase (FIG. 15). An immunoreactive protein of about 85 kDa in size was detected in vAcMNPV.chi (lane 1). Neither the control hemolymph (lane 3) nor hemolymph from larvae infected with vAcMNPV.wt (lane 2) showed any immunoreactive protein. The size of the recombinant protein in hemolymph (lane 1) was the same as the chitinase present in molting fluid of fifth instar *M. sexta* larvae (lane 4).

A chitinase activity assay using glycol chitin as the substrate (Trudel and Asselin, 1989) was performed following native gel electrophoresis of hemolymph from *M. sexta* larvae infected with vAcMNPV.chi (FIG. 16). *M. sexta* molting fluid was used as a positive control (lane 1). This experiment showed that vAcMNPV.chi expressed active chitinase in vivo (lane 2).

In more detail, FIGS. 15 and 16 include a western blot analysis (FIG. 15) and chitinase activity assay (FIG. 16) from hemolymph of fourth instar *M. sexta* larvae virally infected with vAcMNPV.wt or vAcMNPV.chi. In FIG. 15, lane 1 includes recombinant hemolymph; lane 2 includes wild-type hemolymph; lane 3 includes uninfected hemolymph; and lane 4 includes molting fluid from fifth instar *M. sexta* larvae. In FIG. 16, lane 1 includes molting fluid; and lane 2 includes recombinant hemolymph.

FIG. 17 serves to demonstrate the effect of infection with vAcMNPV.wt or vACMMNPV.chi on mortality (FIG. 17) of fourth instar *S. frugiperda* larvae.

The $LT_{50}$, which is the time at which 50% of the larvae died, was compared between recombinant and wild-type virus-injected larvae. The $LRT_{50}$ which is the ratio of times when 50% of the larvae had died after infection with the recombinant or the wild-type (Bonning and Hammock, 1993) was 0.78, demonstrating that the recombinant virus killed the larvae in 75% of the time period required for the wild-type virus to cause mortality (Table 3).

TABLE 1

Carbohydrate Composition of *M. sexta* Wild-Type and Recombinant Chitinases.*

| | Chitinase** | |
|---|---|---|
| Carbohydrate | Native | Recombinant |
| Glucose | 9.0 | 14.6 |
| N-Acetylgalactosamine | 8.2 | 3.7 |
| N-Acetylglucosamine | 3.1 | 2.1 |
| Mannose | 2.7 | 2.9 |
| Galactose | 0.9 | 4.0 |
| Total | 23.9 | 27.3 |

Values were determined by GC-mass spectrometry and are expressed as percentages of sample weight.
**The native enzyme was isolated from pharate pupal molting fluid and the recombinant protein from a baculovirus-insect cell line (Hi-5) gene expression system.

TABLE 2

Chitinase Expression in Media From Baculovirus Infected Cell Lines

| Cell Line | Sample | Activity* $A_{550}$/h/ml medium) |
|---|---|---|
| SF9 | Uninfected | 0.19 |
| | vAcMNPV.wt | 0.16 |
| | vAcMNPV.chi | 0.67 |
| SF21 | Uninfected | 0.28 |
| | vAcMNPV.wt | 0.25 |
| | vAcMNPV.chi | 1.95 |
| Hi-5 | Uninfected | 0.29 |
| | vAcMNPV.wt | 0.45 |
| | vAcMNPV.chi | 4.80 |

*Chitinase activity was estimated in the medium from cells infected with vAcMNPV.chi or vAcMNPV.wt. Uninfected cells were used as controls. Activity was determined colorimetrically using CM-chitin-RBV as substrate.

TABLE 3

Effect of Wild-Type Baculovirus and Recombinant *M. sexta* Chitinase Gene-Containing Virus on Mortality of *Spodoptera frugiperda*.*

| Experiment # | Virus Type | $LT_{50}$** (h) | $LRT_{50}$*** |
|---|---|---|---|
| 1 | Recombinant | 68 (65–71) | 0.77 |
| | Wild-type | 88 (85–94) | |
| 2 | Recombinant | 65 (64–67) | 0.78 |
| | Wild-type | 83 (81–85) | |

*Infection of fourth instar larvae with $2 \times 10^5$ pfu's of vAcMNPV.chi or vAcMNPV.wt. Treatments were significantly different at the $\alpha = 0.05$ level ($n = 13$ and 14 for recombinant and wild-type virus, respectively, in experiment 1 and $n = 32$ in experiment 2; Fisher exact test).
**Time after infection when 50% mortality occurred as determined by probit analysis. 95% confidence limits given in parentheses.
***Ratio for lethal response times when 50% mortality occurred in insects infected with recombinant versus wild-type virus.

EXAMPLE 20

AGROBACTERIUM-MEDIATED TRANSFORMATION OF TOBACCO PLANTS WITH THE MANDUCA SEXTA CHITINASE GENE

The 1.8 kb EcoRI fragment from the full length *M. sexta* chitinase cDNA Clone 10 was subcloned into the EcoRI site of the vector pMON410 (courtesy of Dr. Frank White, Plant Pathology Department, Kansas State University) after deleting the hygromycin resistance gene using the restriction enzyme SmaI to generate pMON401.chi. A plasmid including the exact chitinase gene sequence used in pMOB401.chi but employing the well-known pBluescript vector has been deposited with the American Type Culture Collection and has been accorded Accession No. 97248. Triparental mating was performed with pMON410.chi, pRK2013 (also courtesy of Dr. Frank White, Plant Pathology Department, Kansas State University; carries the "tra" genes) and LBA4404 (Agrobacterium strain; courtesy of Dr. Frank White, Plant Pathology Department, Kansas State University). After incubation at 28° C. overnight, the bacteria were spread on AB minimal media plates containing spectinomycin at a concentration of 500 µg/mL. After incubation for three days at 28° C., single colonies were picked and grown in liquid nutrient agar ("NA") media containing spectinomycin at a concentration of 500 µg/mL at 28° C. DNA was isolated from this bacterial culture and transformed into JM109 (ATCC JM109; an *E. coli* K-12 strain) using standard protocols. Restriction digestion, using a 10× excess of BamHI, and DNA sequencing were conducted on the resulting chimeric JM109 DNA to confirm that the cloned chimeric inserts were in the correct orientation and then used to transform tobacco leaf discs.

Tobacco (*Nicotina tabacum*) leaf discs were generated using a cork borer. They were surface sterilized using ethanol (70%) and then rinsed with water. Leaf discs were placed in MS104 (Sigma Chemical Co, St. Louis, Mo.) media containing no antibiotic. This allowed the bacteria to infect the tissue. After incubation at 27° C., 12 h day, for one week, the leaf discs were transferred to basal media ("BM") containing kanamycin and carbenicillin at a concentration of 100 and 500 µg/mL respectively. After two weeks, leaf discs were transferred to fresh BM media. Leaf discs started to put forth shoots in about two weeks. Shoots were transferred to BM media containing BAP (benzyladenine), NAA (naphthalene acetic acid) and phytagar in small bottles. The concentrations of antibiotics in this media were reduced to 200 µg/mL for carbenicillin and remained at 100 µg/mL for kanamycin. Two weeks later, shoots were transplanted in fresh media. Transgenic plants were tested for the presence of *Manduca sexta* chitinase by western blot analysis. Untransformed plant (wild-type tobacco) and plants transformed with vector pMON410 were used as controls.

EXAMPLE 21

INSECT BIOASSAYS WITH M. SEXTA LARVAE FEEDING ON TRANSGENIC TOBACCO PLANTS

Figure 18:
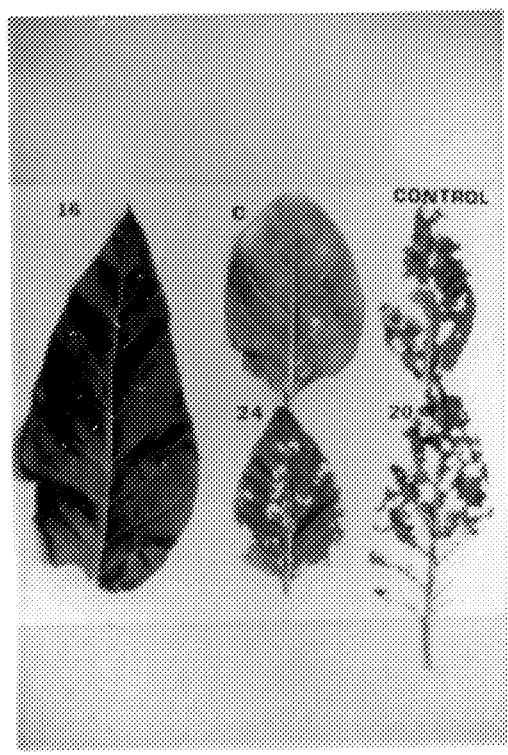
FIG. 18 is a photograph that depicts feeding damage caused by tobacco hornworm on respective control and transgenic tobacco plants expressing insect chitinase.

FIG. 18 depicts the results of insect feeding studies, which confirm that transgenic tobacco plants expressing *M. sexta* chitinase have increased resistance to tobacco hornworms. One control and four transgenic tobacco plants with varying levels of chitinase expression as determined by western blot analysis were chosen. Plants 16 and C had the highest levels, followed by plant 24, and plant 20 had the least. Whereas feeding damage was extensive in the untransformed control plant and plant 20, an intermediate level of damage was observed in the leaf from plant 24 and the least in leaves from plants C and 16.

Figure 19:
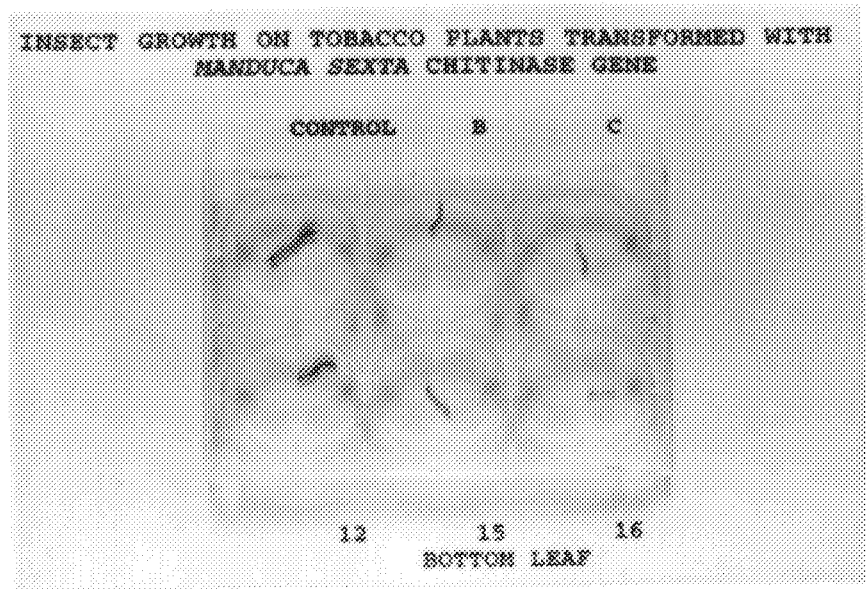
FIG. 19 is a photograph depicting a comparison of insects that fed on respective control and transgenic tobacco plants expressing chitinase.

FIG. 19 depicts, for comparison, insects that fed on control and transgenic tobacco plants expressing chitinase. As compared to larvae reared on control leaves, those reared on plants 12 and 15 showed no growth inhibition and those reared on leaves from plants B, C, and 16 had severe inhibition of growth. In detail, the mean weight of control larvae (n=8–10) was 41.1 mg; the mean weight of larvae on plant 12 was 18.0 mg; on plant B, 9.4 mg; on plant 15, 12.0 mg; on plant C, 6.5 mg; and on plant 16, 7.1 mg. Correlation of increased leaf damage, reduced larval weight and levels of *M. sexta* chitinase expression in the transformed plants demonstrates the insect growth-inhibiting effect of insect chitinase.

EXAMPLE 22

INSECT BIOASSAYS WITH ORYZAEPHILUS MERCATOR LARVAE FEEDING ON WHEAT GERM CONTAINING BACTERIAL, PLANT, OR INSECT CHITINASE

Table 1 illustrates that recombinant insect chitinase is an insecticidal protein when administered orally in the diet whereas bacterial and plant chitinases are not. Larvae of the merchant grain beetle, *Oryzaephilus mercator*, were reared on a diet consisting of raw wheat germ supplemented with either no chitinase, or chitinase of Streptomyces (bacterial chitinase), Serratia (bacterial chitinase), Hordeum (barley chitinase), or Manduca (recombinant insect chitinase). Larvae fed recombinant insect chitinase grew little or not at all while bacterial and plant chitinases were ineffective in controlling larval growth. These results demonstrate that insect chitinase is substantially and unexpectedly more potent as an insect control protein than are chitinases from other sources.

TABLE 4

Effect of chitinases on growth and mortality of the merchant grain beetle, *Oryzaephilus mercator*

| Chitinase* | Larval weight (mg)† | Mortality (%) |
|---|---|---|
| Control | 0.478 ± 0.016 a | 0 |
| Streptomyces (bacteria) | 0.464 ± 0.019 a | 3 |
| Serratia (bacteria) | 0.437 ± 0.062 a | 9 |
| Hordeum (barley) | 0.405 ± 0.053 a | 15 |
| Manduca (insect) | — | 100‡ |

*Enzymes added to raw wheat germ diet at ~ 1–2% level.
†Weight of larvae reared for 13 days. Data are the mean ± SE (n = 4–15). Data with the same letter are not significantly different (α = 0.05) as determined by Tukey statistical analysis.
‡All larvae were dead ≦6 days after egg hatch.

REFERENCES

The following references have been cited above, and are hereby incorporated by reference herein.

Ausubel F. M., Brent R., Kingston R. E., Moore D. D., Seidman J. G., Smith J. A. and Struhl K. (eds) (1987) *Current Protocols in Molecular Biology*, Vol. 1, pp. 1.12.2, 1.13.1, 4.2.3–4.2.4, 5.5.5–5.5.10 and 5.6.1–5.6.8. John Wiley and Sons, New York.

Aviv H. and Leder P. (1972) Purification of biologically active globin mRNA by chromatography on oligothymidylic acid-cellulose. *Proc. Natl. Acad. Sci. U.S.A.* 69, 1408–1412.

Biggin M. D., Gibson T. J. and Hong G. F. (1983) Buffer gradient gels and $^{35}$S label as an aid to rapid DNA sequence determination. *Proc. Natl. Acad. Sci. U.S.A.* 80, 3963–3965.

Bell R. A. and Joachim F. G. (1976) Techniques for rearing laboratory colonies of tobacco hornworms and pink bollworms. *Ann. Ent. Soc. Am.* 69, 365–373.

Blackshear P. J. (1984) Systems for polyacrylamide gel electrophoresis. *Methods in Enzymology* 104, 237–255.

Blin N. and Stafford D. W. (1976) Isolation of high molecular-weight DNA. *Nucl. Acids Res.* 3, 2303–2312.

Bonning C. B. and Hammock B. D. (1993) Lethal ratios: An optimized strategy for presentation of bioassay data generated from genetically engineered baculovirus. *J. Invert. Path.* 62,196–197.

Brookhart G. L. and Kramer K. J. (1990) Proteinases in molting fluid of the tobacco hornworm, *Manduca sexta*. *Insect Biochem.* 20, 467–477.

Bollenbacher W. E., Vedeckis W. V., Gilbert L. I and O'Conner J. D (1975) Ecdysone titers and prothoracic gland activity during the larval-pupal development of *Manduca sexta*. *Dev. Biol.* 44, 46–53.

Broglie K., Chet I., Holliday M., Cressman R., Biddle P., Knowlton S., Mauvais C. J. and Broglie R. (1991) Transgenic plants with enhanced resistance to the fungal pathogen *Rhizoctonia solani*. *Science,* 254, 1194–1197.

Chandra G. R., Albaugh G. P. and Muthukrishnan S. (1985) Methodology for Gene Expression. In *CRC Handbook of Natural Pesticides*: Methods (Edited by Bhushnan Mandava N.), Vol II, pp. 493–523. CRC Press, Florida.

Chirgwin J. M., Przybyla A. E., Macdonald R. J. and Rutter W. J. (1979) Isolation of biologically active ribonucleic acid from sources enriched in ribonucleases. *Biochem.* 18, 5294–5299.

Chrispeels M. J., Raikhel, N. (1991) Lectins, lectin genes, and their role in plant defense. *The Plant Cell* 3, 1–9.

Clark K. L. (1991) Ph.D. Thesis. Sequence alignments without the use of arbitrary parameters. Kansas State University.

Clemens M. J. (1984) Translation of eukaryotic messenger RNA in cell-free extracts. In *Transcription and Translation* (Edited by Hames B. D. and Higgins S. J.), The Practical Approach Series, pp. 231–270. IRL Press, England.

Corpuz L. M., Choi H., Muthukrishnan S. and Kramer K. J. (1991) Sequences of two cDNAs and expression of the genes encoding methionine-rich storage proteins of *Manduca sexta*. *Insect Biochem.* 21, 265–276.

Daum R. J. (1970) A revision of two computer programs for probit analysis. *Bull. Entomol. Soc. Am.* 16, 10–15.

Eldridge R., O'Reilly D. R. and Miller L. K. (1992) Efficacy of a baculovirus pesticide expressing an occlusion hormone gene. *Biol. Control* 2, 104–110.

Fukamizo T. and Kramer K. J. (1985a) Mechanism of chitin oligosaccharide hydrolysis by the binary chitinase system in insect molting fluid. *Insect Biochem.* 15, 1–7.

Fukamizo T. and Kramer K. J. (1985b) Mechanism of chitin hydrolysis by the binary chitinase system in insect molting fluid. *Insect Biochem.* 15, 141–145.

Fukamizo T. and Kramer K. J. (1987) Effect of 20-hydroxyecdysone on chitinase and N-acetylglucosaminidase during the larval-pupal transformation of *Manduca sexta* (L). *Insect Biochem.* 17, 547–550.

Henrissat B. (1990) Weak sequence homologies among chitinases detected by clustering analysis. *Protein Seq. Data Anal.* 3, 523–526.

Harpster M. H. and Dunsmuir P. (1989) Nucleotide sequence of the Chitinase B gene of *Serratia marcescens* QMB1466. *Nucl. Acids Res.* 17, 5395.

Jones J. D. G., Grady K. L., Suslow T. V. and Bedbrook J. R. (1986) Isolation and characterization of genes encoding two chitinase enzymes from *Serratia marcescens*. *EMBO J.* 5, 467–473.

Kamei K., Yamamura Y., Hara S. and Ikenaka T. (1989) Amino acid sequence of chitinase from *Streptomyces erythraeus*. *J. Biochem.* 105, 979–985.

Kimura S. (1973) The control of chitinase activity by ecdysterone in larvae of *Bombyx mori*. *J. Insect Physiol.* 19, 115–123.

Koga D., Mai M.S., Dziadik-Turner C. and Kramer K. J. (1982) Kinetics and mechanism of exochitinase and -N-acetylglucosaminidase from the tobacco hornworm, *Manduca sexta L*. *Insect Biochem.* 12, 493–499.

Koga D., Jilka J. and Kramer K. J. (1983a) Insect endochitinases: Glycoproteins from molting fluid, integument and pupal hemolymph of *Manduca sexta L*. *Insect Biochem.* 13: 295–305.

Koga D., Mai M. S. and Kramer K. J. (1983b) Comparative biochemistry of insect exo-N-acetylglucosaminidases: Characterization of a third enzyme from pupal hemolymph of the tobacco hornworm, *Manduca sexta L*. *Comp. Biochem. Physiol.* 74B: 515–520.

Koga D., Fujimoto H., Funakoshi T., Utsumi T. and Ide A. (1989) Appearance of chitinolytic enzymes in integument of *Bombyx mori* during the larval-pupal transformation. Evidence for zymogenic forms. *Insect Biochem.* 19, 123–128.

Koga D., Funakoshi T., Mizuki K., Ide A., Kramer K. J., Zen K. C., Choi H. and Muthukrishnan, S. (1992) Immunoblot analysis of chitinolytic enzymes in integuments and molting fluids of the silkworm, *Bombyx mori*, and the tobacco hornworm, *Manduca sexta*. *Insect Biochem.* 19, 123–128.

Kramer K. J., Dziadik-Turner C. and Koga D. (1985) Chitin metabolism in insects. In *Comprehensive Insect Physiology, Biochemistry and Pharmacology* (Edited by Kerkut G. A. and Gilbert L. I.), Vol. 3, pp. 75–115. Pergamon Press, New York.

Kramer K. J. and Koga D. (1986) Insect chitin: physical state, synthesis, degradation and metabolic regulation. *Insect Biochem.* 16, 851–877.

Kuranda M. J. and Robbins P. W. (1991) Chitinase is required for cell separation during growth of *Saccharomyces cerevisiae*. *J. Biol. Chem.* 266, 19758–19767.

Laemmli U. K. (1970) Cleavage of structural proteins during the assembly of the head of bacteriophage $T_4$. *Nature* (London) 227, 680–685.

Maniatis T., Fritsch E. F. and Sambrook J. (1982) *Molecular Cloning. A Laboratory Manual,* 545 pp. Cold Spring Harbor Laboratory, New York.

Matsudaira P. (1987) Sequence from picomole quantities of proteins electro-blotted onto polyvinylidene difluoride membranes. *J. Biol. 10035–10038*.

Mawhinney T. P., Feather M. S., Barberc G. J. and Martinez J. R. (1980) The rapid, quantitative determination of neutral sugars and amino sugars in glycoproteins by gas-liquid chromatography. *Anal. Biochem.* 101, 112–117.

Mawhinney T. P. (1986) The simultaneous determination of N-acetyl-glucosamine, N-acetylgalactosamine, N-acetylglucosaminitol and N-acetylgalactoaminitol by gas-liquid chromatography. *J. Chromatogr.* 351, 91–102.

Metraux J. P., Burkhart W., Moyer M., Dincher S., Middlesteadt W., Williams S., Payne G., Carnes M. and Ryals J. (1989) Isolation of a complementary DNA encoding a chitinase with structural homology to a bifunctional lysozyme/chitinase. *Proc. Natl. Acad. Sci.* 86, 896–900.

Miller J. S., Paterson B. M., Ricciardi R. P., Cohen L. and Roberts B. E. (1983) Methods using cell-free protein synthesizing systems for the identifica- tion of recombinant DNA molecules. *Methods Enzymol.* 101, 651–675.

Mitsui T. and Riddiford L. M. (1976) Pupal cuticle formation by *Manduca sexta* epidermis in vitro: patterns of ecdysone sensitivity. *Dev. Biol.* 54, 172–186.

Passanneau J. V. and Williams C. M. (1953) The moulting fluid of Cecropia silkmoth. *J. Exp. Biol.* 246, 124–131.

Riddiford L. M. (1987) Hormonal control of sequential gene expression in insect epidermis. In *Molecular Entomology, UCLA Symposium Mol. Cell Biol., New Series* (Edited by Law J.), Vol. 49, pp. 211–222. Alan R. Liss, New York.

Riddiford L. M. (1985) Hormone action at the cellular level. In *Comprehensive Insect Physiology, Biochemistry and Pharmacology* (Edited by Kerkut G. A. and Gilbert L. I.), Vol. 8, pp. 37–85. Pergamon Press, New York.

Robbins P. W., Trimble R. B., Wirth D. F., Hering C., Maley F., Maley G. F., Das R., Gibson B. W., Royal N. and Biemann K. (1984) Primary structure of the Endo-β-N-acetylglucosaminidase H. *J. Biol. Chem.* 259, 7577–7583.

Samac D. A., Hironaka C. N., Yallaly P. E. and Shah D. M. (1990) Isolation and characterization of the genes encoding basic and acidic chitinase in *Arabidopsis thaliana*. *Plant Physiol.* 93, 907–914.

Sanger F., Nicklen S. and Coulson A. R. (1977) DNA sequencing with chain-terminating inhibitors. *Proc. Natl. Acad. Sci. U.S.A.* 74, 5463–5467.

Shinshi H., Neuhaus J., Ryals J., and Meins F. (1990) Structure of a tobacco endochitinase gene: evidence that different chitinase genes can arise by transposition of sequences encoding a cysteine-rich domain. *Plant Mol. Biol.* 14: 357–368.

Spindler-Barth M., Shaaya E. and Spindler K. D. (1986) The level of chitinolytic enzymes and ecdysteroids during larval-pupal development in *Ephestia cautella* and their modification by a juvenile hormone analogue. *Insect Biochem.* 16, 187–190.

Summers M. D. and Smith G. E. (1987) A manual of methods for baculovirus vectors and insect cell culture procedures. Texas Agricultural Experiment Station Bulletin No. 1555.

Tabor S. and Richardson C. C. (1987) DNA sequence analysis with a modified bacteriophage T7 DNA polymerase. *Proc. Natl. Acad. Sci. U.S.A.* 84, 4767–4771.

Tempst P. and Riviere L. (1989) Examination of automated polypeptide sequencing using standard phenyl isothiocyanate reagent and subpicomole high performance liquid chromatographic analysis. *Anal. Biochem.* 183, 290–300.

Tilley K. A., Lookhart G. L., Hoseney R. C. and Mawhinney T. P. (1993) Evidence for glycosylation of the high molecular weight glutenin subunits 2, 7, 8, and 12 from Chinese spring and TAM 105 wheats. *Cereal Chemistry.* 70 (5), 602–606.

Thomas P. (1980) Hybridization of denatured RNA and small DNA fragments transferred to nitrocellulose. *Proc. Natl. Acad. Sci. U.S.A.* 77, 5201–5205.

Trudel J. and Asselin A. (1989) Detection of chitinase activity after polyacrylamide gel electrophoresis. *Analyt. Biochem.* 178, 362–366.

Vail P. V. (1993) Viruses for control of arthropod pests. In *Pest Management: Biologically Based Technologies* (R. D. Lumsden and J. L. Vaughn, Eds.) Amer. Chem. Soc. Conference Proceedings Series, pp. 30–39.

Watanabe T., Oyanagi W., Suzuki K. and Tanaka H. (1990) Chitinase system of *Bacillus circulans* WL-12 and importance of chitinase A1 in chitin degradation. *J. Bacteriol.* 172, 4017–4022.

Watanabe T., Oyanagi W., Suzuki K., Ohnishi K. and Tanaka H. (1992) Structure of the gene encoding Chitinase D of *Bacillus circulans* WL-12 and possible homology of the enzyme to other prokaryotic chitinases and Class III plant chitinases. *J. Bacteriol.* 174, 408–414.

Winston S., Fuller S. and Hurrel J. (1987) Western Blotting. In: *Current Protocols in Molecular Biology*, John Wiley, New York.

---

We claim:

1. An isolated oligonucleotide encoding an insect chitinase having insecticidal activity, said chitinase having an active site with the sequence of the amino acids 136–148 of SEQ. ID. No. 2.

2. The oligonucleotide of claim 1, said chitinase having at least a 50% amino acid sequence similarity to the protein encoded by SEQ ID No. 1.

3. The digonucleotide of claim 1, said oligonucleotide encoding the protein encoded by Sequence ID No. 1.

4. The digonucleotide of claim 1, said oligonucleotide comprising the coding region of Sequence ID No. 1.

5. The oligonucleotide of claim 1, said oligonucleotide being a cDNA.

6. A chimeric vector comprising an oligonucleotide encoding an insect chitinase having insecticidal activity, said chitinase having an active site with the sequence of the amino acids 136–148 of Seq. Id. No. 2.

7. The vector of claim 6, said chitinase having at least 50% amino acid sequence similarity to the protein encoded by Sequence ID No. 1.

8. The vector of claim 6, said oligonucleotide encoding the protein encoded by Sequence ID No. 1.

9. The vector of claim 6, said oligonucleotide comprising the coding region of Sequence ID No. 1.

10. The vector of claim 6, said oligonucleotide being a cDNA.

11. The vector of claim 6, said vector being an *Agrobacterium tumefaciens* vector.

12. The vector of claim 11, said oligonucleotide encoding the protein encoded by Sequence ID No. 1.

13. The vector of claim 11, said oligonucleotide comprising the coding region of Sequence ID No. 1.

14. A transgenic plant having a genome comprising an oligonucleotide encoding an insect chitinase having insecticidal activity, said chitinase having an active site with the sequence of the amino acids 136–148 of Seq. Id. No. 2.

15. The plant of claim 14, said chitinase having a least 50% amino acid sequence similarity to the protein encoded by SEQ ID No. 1.

16. The plant of claim 14, said oligonucleotide encoding the protein encoded by Sequence ID No. 1.

17. The plant of claim 14, said oligonucleotide comprising the coding region of Sequence ID No. 1.

18. The plant of claim 14, said plant being tobacco.

19. A method of controlling insect, fungal or nematode pests comprising the steps of:
(a) growing a transgenic plant having a genome comprising an oligonucleotide encoding an insect chitinase having insecticidal activity, said chitinase having an active site with the sequence of the amino acids 136–148 of Seq. Id. No. 2; and
(b) allowing said pests to eat portions of said plant.

20. The method of claim 19, said chitinase having at least 50% amino acid sequence similarity to the protein encoded by SEQ ID No. 1.

21. The method of claim 19, said oligonucleotide encoding the protein encoded by Sequence ID No. 1.

22. The method of claim 19, said oligonucleotide comprising the coding region of Sequence ID No. 1.

23. The method of claim 19, said plant being tobacco.

24. The plant of claim 14, said plant being a cereal grain.

25. The method of claim 19, said pests being insects.

26. The method of claim 19, said plant being a cereal grain.

27. An isolated gene from *Manduca sexta* which encodes insecticidal chitinase.

28. A transgenic plant having a genome comprising an oligonucleotide encoding the protein encoded by SEQ ID No. 1.

29. An isolated oligonucleotide encoding the protein encoded by SEQ ID No. 1.

30. An isolated oligonucleotide comprising the coding region of SEQ ID No. 1.

31. A chimeric vector comprising an oligonucleotide encoding an insect chitinase having insecticidal activity, said chitinase having an active site with the sequence of the amino acids 136–148 of Seq. Id. No. 2, said vector being the plasmid deposited as ATCC A No. 97248.

* * * * *